Figure 1:
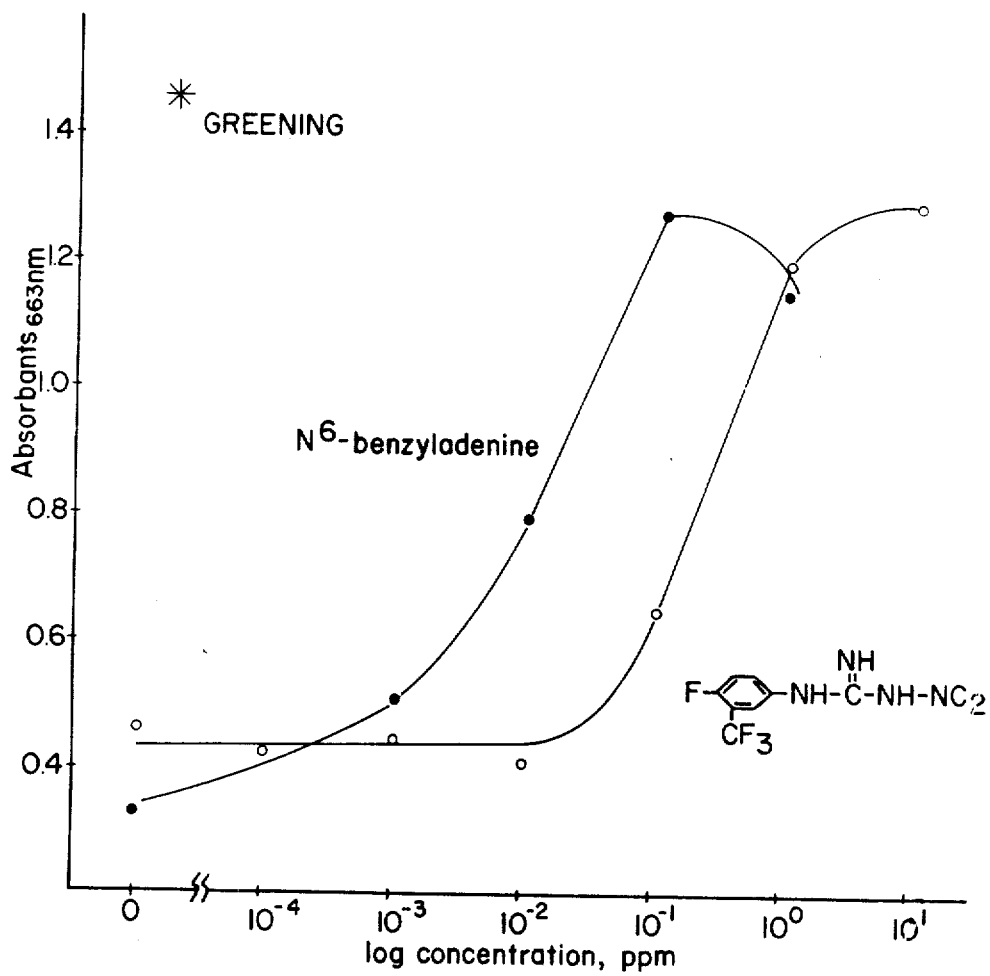
Figure 2:
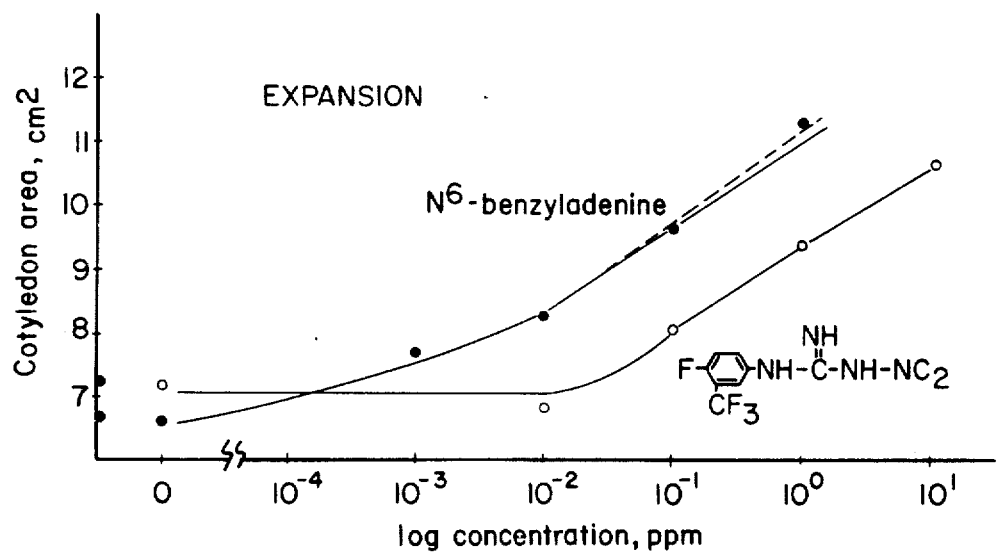

United States Patent [19]

Speltz et al.

[11] Patent Number: 4,804,780

[45] Date of Patent: Feb. 14, 1989

[54] SUBSTITUTED NITRO AND CYANOGUANIDINES

[75] Inventors: Laurine M. Speltz, Princeton; Bryant L. Walworth, Pennington; Alexander D. Pavlista, Lawrenceville, all of N.J.

[73] Assignee: American Cyanamid Company, Stamford, Conn.

[21] Appl. No.: 835,847

[22] Filed: Mar. 3, 1986

Related U.S. Application Data

[60] Division of Ser. No. 551,611, Nov. 17, 1983, Pat. No. 4,594,092, which is a continuation-in-part of Ser. No. 451,698, Dec. 20, 1982, abandoned.

[51] Int. Cl.[4] .......................................... C07C 129/14
[52] U.S. Cl. .................................. 564/104; 564/108; 564/237; 564/238; 549/426; 560/135; 562/439; 71/88; 71/98; 71/105; 71/111; 71/121
[58] Field of Search ...................... 71/121, 88, 77, 68; 564/105, 108, 104; 549/419, 426; 558/391, 419, 422; 514/609, 610, 451, 460

[56] References Cited

U.S. PATENT DOCUMENTS 2,946,820  7/1960  Henry et al. ...................... 564/108

FOREIGN PATENT DOCUMENTS 0519448  12/1955  Canada ............................. 564/108
2147881   3/1973  France .
2340723   9/1977  France .

OTHER PUBLICATIONS

Tilley, et al., "The Synthesis of 3,5-Diamino-1,2,4-Oxa-Diazoles", Helvetica Chimica Acta, vol. 63(4), 1980, pp. 841–859.
Koshinuma, et al., "Screening Test on Anticancer and Antimicrobial Actions", (CA 76 No. 67w.) Eisei Shikenjo Hokoku 1970, 18(88) 118–123.
Warner, et al., "Quantitative Structure–Activity Relation-Ships for Biguanides . . . ", Journal Medicinal Chem., vol. 22(4), 1979, pp. 359–366.
McKay, "Preparation of N-Substituted-N-Nitroguanidines, etc., " J. Amer. Chem. Soc., vol. 71, pp. 1968–1970 (1949).
Fishbein et al., "Preparation and Reactions of 2-Alkyl-, etc., "J. Amer. Chem. Soc., vol. 76, pp. 1877–1878 (1954).
Pozsar et al., "Preparation with Cytokinin-Type, etc.," Chem. Abstr. 97:87045t (1982).

*Primary Examiner*—Glennon H. Hollrah
*Assistant Examiner*—A. A. Owens
*Attorney, Agent, or Firm*—John W. Hogan, Jr.

[57] ABSTRACT

Novel substituted phenyl and benzyl nitroguanidine and phenyl and benzyl cyanoguanidine compounds. Methods for increasing crop yield, inhibiting lodging of graminaceous crops, and inducing cytokinin-like responses in crop plants with said novel guanidine compounds and derivatives thereof, as well as methods for inhibiting deterioration and/or extending the shelf life of harvested fruit, vegetables, and ornamentals are disclosed.

15 Claims, 2 Drawing Sheets

* Greening = chlorophyll biosynthesis
† nm = nanometer

* $N^6$-BA = $N^6$-benzyladenine
† Guanidine = 1-nitro-3-($\alpha,\alpha,\alpha$,4-tetrafluoro-m-tolyl)-guanidine

SUBSTITUTED NITRO AND CYANOGUANIDINES

This is a divisional application of U.S. patent application Ser. No. 551,611, filed Nov. 17, 1983, now U.S. Pat. No. 4,594,092, which in turn is a continuation-in-part of U.S. patent application Ser. No. 451,698, filed Dec. 20, 1982, abandoned.

The present invention relates to certain novel nitro and cyanoguanidine compounds. Additionally, the invention relates to the use of certain guanidines useful in a variety of plant-growth regulating activities.

The guanidine compounds of the present invention include novel substituted phenyl and benzyl nitroguanidines and novel phenyl and benzyl cyanoguanidines. Although nitro and cyanoguanidines are disclosed in the art, the presently-described compounds are novel.

In addition to the novel compounds of the present invention, it has been unexpectedly discovered that certain guanidines possess heretofore undisclosed plant growth regulating activities. These plant growth regulating actions include increases of certain crop yields, as well as inhibition in deterioration of harvested crops and ornamentals.

It is an object of the present invention, therefore, to provide the novel nitro and cyanoguanidines described more fully below.

It is a further object of this invention to disclose methods of using certain guanidines as plant growth regulants. Furthermore, these guanidines exhibit growth regulating activities in such fashion as increasing crop yields and inhibiting deterioration of harvested crops and ornamentals.

These and other objects of the present invention will become clearer by the more detailed description of the invention which follows.

The invention described herein relates to novel nitro and cyanoguanidine compounds represented by the following structural formulae (I–IV):

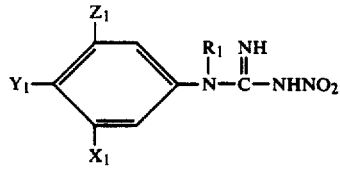
(I)

wherein $X_1$ is $COCH_3$, halogen, CN, $CH_2CN$, $C(OH)_2CF_3$, $OCHF_2$, $OCF_3CH_3$, $SCH_3$, $CF_3$, $NO_2$, $OCF_2CHF_2$, $OCH_3$, $N(CH_3)_2$, $COOCH_3$ or $CH_2OR_3$, where $R_3$ is H or $CH_3$; $Y_1$ is H, halogen, or $CH_3$; $Z_1$ is H, $CH_3$, halogen, $OCH_3$ or $CF_3$; $R_1$ is H or $CH_3$; with the provisos that when $X_1$ is $CH_3$, $OCH_3$, F, Cl or Br and R is H, then $Y_1$ and $Z_1$ cannot both be hydrogen; and when $X_1$ is Cl and $Z_1$ and R are each hydrogen, then $Y_1$ cannot be methyl; and the salts or tautomers thereof;

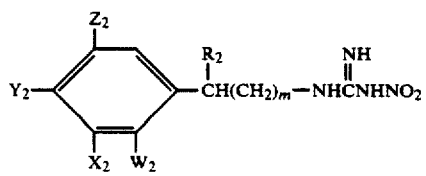
(II)

wherein $X_2$ is H, OH, straight or branched $C_1$–$C_4$ alkoxy, $SCH_3$, halogen, $OCF_3$, $CF_3$, straight or branched $C_1$–$C_4$ and alkyl or

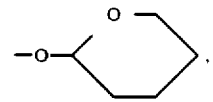

tetrahydro-2H-pyran-2-yl; $Y_2$ is H or F; $Z_2$ is F, H, $CH_3$ or $OCH_3$; $W_2$ is H or F; m is an integer of 0, 1 or 2; $R_2$ is H, $CH_3$, $C_2H_5$ or $CF_3$; with the provisos that when m is 0 and $R_2$ is H or $CH_3$, then $W_2$, $X_2$, $Y_2$ and $Z_2$ cannot all be hydrogen; and when m is 1, then $R_2$, $W_2$, $X_2$, $Y_2$ and $Z_2$ cannot all be hydrogen; and the salts or tautomers thereof;

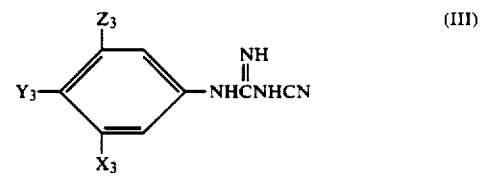
(III)

wherein $X_3$ is $OCH_3$, $CH_3$, halogen or $CF_3$; $Y_3$ is H, OH or halogen and $Z_3$ is H or Cl; with the provisos that $Y_3$ and $Z_3$ can both be hydrogen only when $X_3$ is $OCH_3$; and when $X_3$ and $Y_3$ are each Cl, Br or I, then $Z_3$ cannot be hydrogen; and when $X_3$ is $CH_3$ and $Z_3$ is H, then $Y_3$ cannot be Cl; and the salts or tautomers thereof; and

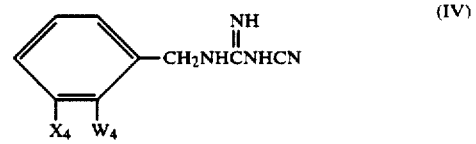
(IV)

wherein $W_4$ is H or F; $X_4$ is straight or branched $C_1$–$C_4$ alkoxy, straight or branched $C_1$–$C_4$ alkyl or F; with the provisos that when $W_4$ is F, $X_4$ is H; and the salts or tautomers thereof.

Among the salt preparations of the present substituted guanidines are included the inorganic alkali metal, alkaline earth metal, Co, Cu, Zn, and Ag salts, along with the organic amine salts represented by the structure, $\overset{+}{N}R_aR_bR_cR_d$, wherein $R_a$, $R_b$, $R_c$, and $R_d$ are each selected from hydrogen and alkyl $C_1$–$C_{30}$ straight or branched chain and optionally substituted with one or two —OH, $C_3$–$C_6$ alkenyl or $C_3$–$C_6$ alkynyl groups. Preferred salts of these compounds include the sodium, calcium, magnesium, potassium, ammonium, methylamine, trimethylamine, dodecylamine, tributylamine, diisopropylamine, triethylamine, tetrabutylamine, and tallow-amine salts.

The substituted phenylnitroguanidines of the present invention depicted by formula (I) above can be prepared by reaction of an appropriately-substituted aniline with approximately an equimolar amount of an N-alkyl-N-nitroso-N'-nitroguanidine in the presence of an aqueous alcoholic solution. The mixture is then heated to about 40° C., treated with a strong base such as sodium hydroxide, and the alcohol removed from the mixture by evaporation. The remaining liquid is then filtered, and the filtrate acidified with a strong mineral acid (i.e., hydrochloric acid) to yield the desired formula (I) substituted phenylnitroguanidine. This reaction is graphically illustrated as follows:

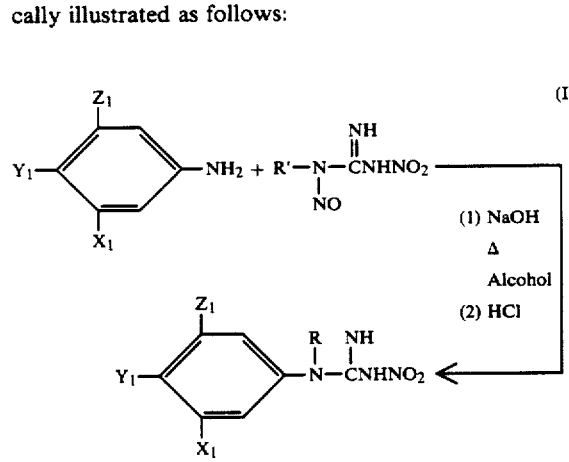

wherein R' is $C_1$–$C_4$ alkyl; R is hydrogen and $X_1$, $Y_1$, and $Z_1$ are as described above. (See McKay and Wright [*Journal American Chemical Society*, 71: 1968 (1949)]).

Conversion of the above-identified formula (I) substituted phenylnitroguanidine to the corresponding 2-methyl derivative can be achieved by reaction of the substituted phenylnitroguanidine in which R is hydrogen, with methyl iodide and silver oxide or sodium hydroxide at an elevated temperature. The reaction is graphically illustrated as follows:

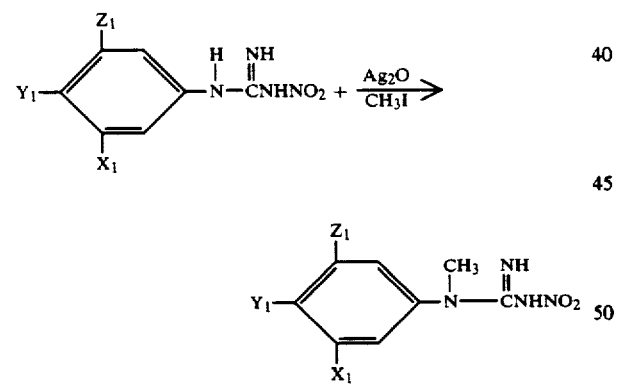

wherein $X_1$, $Y_1$, and $Z_1$ are as described above.

The formula (II) substituted benzylnitroguanidines may be prepared in the same manner as described for the preparation of the formula (I) substituted phenylnitroguanidines excepting that the appropriately-substituted benzylamine is substituted for the aniline. Alternatively, the compounds of formula (II) can be prepared by reacting the benzylamine with nitroguanidine as shown. The product is collected by filtration and recrystallized from the appropriate solvent.

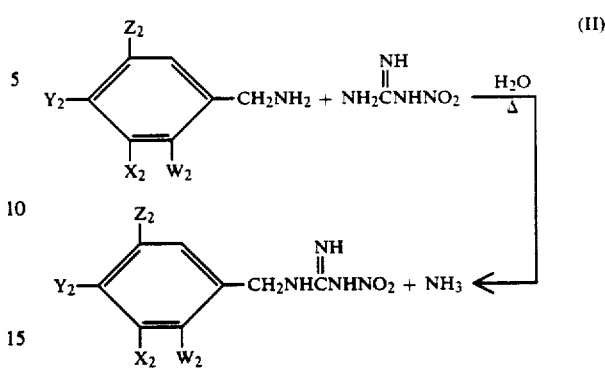

wherein $X_2$, $Y_2$, $Z_2$, and $W_2$ are as described above. (See Davis and Abrams [*Proc. Am. Acad. Arts Sci.*, 61: 437 (1926)]).

The formula (II) benzylnitroguanidines may also be prepared by reaction of the appropriately-substituted benzylamine with an essentially equivalent amount of a 2-alkyl-1(or 3)-nitro-2-thiopseudourea to produce the formula (II) substituted benzylnitroguanidines. Use of a solvent such as ethanol in this reaction is optional. (See Fishbein and Gallahan [*Journal American Chemical Society*, 76: 1877 (1954)] which is illustrated as follows:

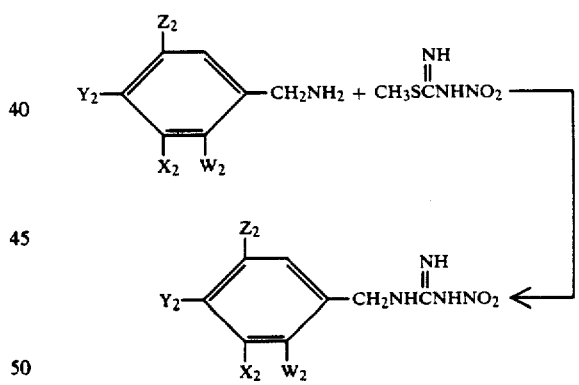

wherein $X_2$, $Y_2$, $Z_2$, and $W_2$ are as described above.

Preparation of the substituted phenyl and benzyl cyanoguanidines (III and IV) is readily accomplished by dissolving or dispersing the appropriately-substituted aniline or benzylamine in hydrochloric acid and admixing the thus-formed solution or dispersion with an equimolar amount of sodium dicyanamide. In practice, it is generally desirable to disperse the sodium dicyanamide in water prior to admixture with the aniline solution or to disperse the sodium dicyanamide in ethoxyethanol for reaction with the benzylamine. This reaction is illustrated as follows:

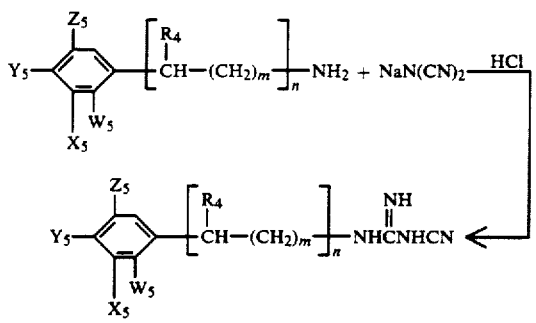

wherein $R_4$, $X_5$, $Y_5$, $Z_5$, $W_5$, m, and n are as previously described.

The present invention also relates to methods for regulating plant growth and in particular, for increasing crop yield of underground stem crops, underground stem ornamentals, root crops, graminaceous crops, forage crops, tomatoes, tobacco, sunflowers, cotton, cucurbits, and fruit. This method involves application to the foliage of subject plants or to soil containing the seeds or other propagating organs thereof of a crop-yield-enhancing amount of a compound having the following structural formula (V):

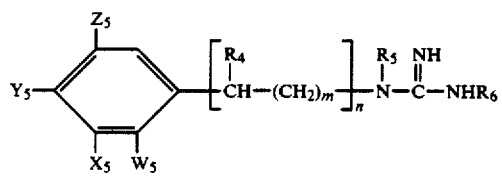

(V)

wherein $W_5$ is H, F or Cl; $X_5$ is H, straight or branched $C_1$-$C_4$ alkyl, halogen, CN, $NO_2$, $CH_2CH$. $OCHF_2$, $OCF_2CHF_2$, $OCF_3$, $CF_3$, $C_1$-$C_4$ alkoxy,

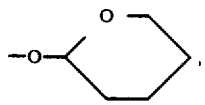

tetrahydro-2H-pyran-2-yl, OH, $C(OH)_2CF_3$, $SCH_3$, $COCH_3$, $N(CH_3)_2$, $COOCH_3$ or $CH_2OR_3$, where $R_3$ is H or $CH_3$; $Y_5$ is H, OH, $OCH_3$, $CH_3$ or halogen; $Z_5$ is H, $CH_3$, halogen, $OCH_3$ or $CF_3$; $R_4$ is H, $CH_3$, $C_2H_5$ or $CF_3$; $R_5$ is H or $CH_3$; $R_6$ is $NO_2$ or CN; m is an integer of 0, 1 or 2; n is an integer of 0 or 1; and the salts or tautomers thereof.

Compounds depicted by formula (V) above in which $X_5$ is a substituent other than hydrogen; $Y_5$, $Z_5$, n, $R_5$, and $R_6$ are as described above; m is 0 or 1; $R_4$ is H; and $W_5$ is H, represent preferred crop-yield-enhancing compounds of the present invention. Especially preferred compounds which enhance crop yields are the phenyl compounds depicted by formula (V), wherein n is 0; $X_5$ is $CH_3$, halogen, $CF_3$, $OCF_3$, $OCHF_2$, $C(OH)_2CF_3$, or $COCH_3$; $Y_5$ is H, halogen, or $CH_3$; $Z_5$ is H, $CH_3$, $OCH_3$, or halogen; $R_5$ is H; $R_6$ is $NO_2$; and $W_5$ is H; provided that when $X_5$ is chloro and $Z_5$ is hydrogen, $Y_5$ cannot be methyl; and the pharmaceutically-acceptable salts or tautomers thereof.

Yet another preferred group of crop-yield-enhancing compounds of the invention includes the benzyl compounds depicted by formula (V), wherein n is 1; $X_5$ is H, $OCH_3$, $CH_3$ or halogen; $Y_5$ is H, F or $OCH_3$; $Z_5$ is hydrogen; $R_5$ is H; $R_6$ is $NO_2$; m is 0; $R_4$ is H or $CH_3$; and $W_5$ is H.

In addition to the plant-growth-regulating and crop-yield-enhancing actions of the formula (V) compounds, these compounds surprisingly are found to be useful for preserving the freshness and/or inhibiting deterioration of harvested crops, particularly recently-harvested green fruit, vegetables, and leafy ornamentals, especially recently-harvested edible leafy vegetables such as lettuce, spinach, beet greens, endive, swiss chard, escarole, and chickory.

The above-described procedures for the preparation of the formula (I) substituted phenylnitroguanidines and formula (II) substituted benzylnitroguanidines are likewise useful for the preparation of the variously substituted formula (V) nitroguanidines using the appropriate aniline or amine. The reaction may be illustrated as follows:

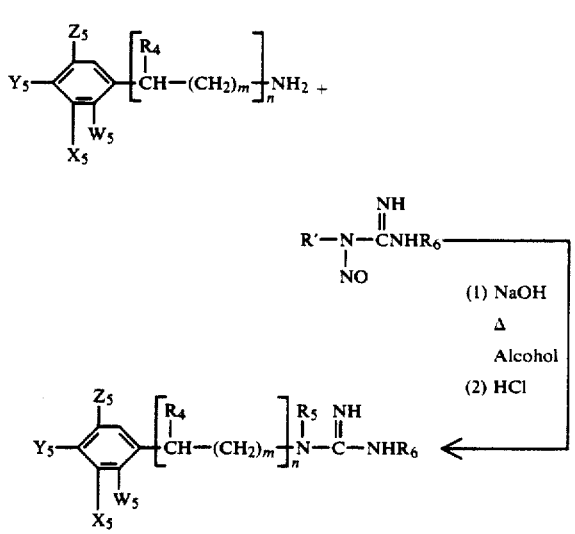

wherein $R_6$ is $NO_2$; $R_5$ is H; and $R_4$, m, n, $W_5$, $X_5$, $Y_5$, and $Z_5$ are as described above.

In practice, it has been found that the formula (V) substituted guanidines of the present invention are highly effective crop-yield-enhancing agents when applied in effective amounts to the foliage of crops or to soil containing seeds or other propagating organs, such as corms, rhizomes, bulbs, or seed pieces thereof. Moreover, it has been found that the formula (V) compounds of this invention are especially effective for increasing crop yield of underground stem crops, underground stem ornamentals, root crops, graminaceous crops, forage crops, tomatoes, tobacco, sunflowers, cotton, cucurbits, and fruit; and, further, that crop-yield enhancement can be achieved with both solid and liquid formulations containing the biologically-active formula (V) substituted guanidine.

Surprisingly, it has also been discovered that the application of a formula (V) substituted guanidine to the foliage of the above-said crops or to soil containing seeds or other propagating organs thereof, in an amount sufficient to provide about 0.06 to 5.0 kg/hectare (preferably about 0.125 to 2.0 kg/hectare), causes the treated plants to increase the size and/or the number of the tubers, corms, rhizomes, bulbs, kernels, gourds, bolls, or fruit produced thereby. Additionally, it is noted that treatment of underground stem crops, underground stem ornamentals, or root crops with the formula (V) guanidine compounds of the present invention markedly improves uniformity in size and shape of the tubers, corms, rhizomes or bulbs produced by the treated plants. These results are especially noticeable in potato crops (e.g., white potatoes) wherein treated plants are found to produce: (1) a greater number of potatoes, (2) a substantially increased total weight of potatoes, (3) more superior grade Number 1 potatoes, and (4) fewer Number 2 potatoes.

When the formula (V) substituted guanidines are to be applied to harvested fruit, vegetables, or ornamentals to inhibit their deterioration and improve their freshness and shelf life, the formula (V) substituted guanidine is dissolved in water, about 0.01 to 800.0 ppm, and applied as an aqueous solution in the form of a dip or a spray to the fruit, vegetable, or ornamental which is to be protected. For best results, the fruit, vegetables, or ornamentals which are to be protected against rapid deterioration may be sprayed with the aqueous solution containing from 0.01 to 800.0 ppm of the formula (V) substituted guanidine about one to two days before harvest and then either sprayed or dipped in the aqueous solution of the formula (V) guanidine again within about 24 hours following harvest. If multiple applications are impractical, the harvested crop may be dipped or sprayed with an aqueous solution of active ingredient shortly after harvest (preferably within 24 hours following harvest).

It has also been found that application of the formula (V) substituted guanidines to the foliage of graminaceous crops such as rice, at the panicle development stage, inhibits lodging of the rice due to adverse weather conditions.

The remarkably unique plant-growth-regulant activity of the formula (V) compounds of the present invention is further demonstrated by the physiological alterations noted in tobacco plants that have been treated prior to maturation, preferably between the early seedling stage and plant topping, with a formula (V) substituted guanidine compound. When tobacco plants, approximately 5 to 125 centimeters in height, are treated with about 0.025 to 2.50 kg/hectare (preferably 0.1 to 0.3 kg/hectare) of a formula (V) substituted nitro or cyanoguanidine, senescence in the lower, more mature, tobacco leaves is delayed or retarded until senescence in essentially all of the leaves of the treated plant begins. Thus, harvesting of the mature tobacco leaves can be completed in a single, or in at most, two cuttings, whereas, it had not been uncommon in the past to require three or four cuttings.

In addition to these advantages, it is also noted that tobacco plants treated with the formula (V) nitro or cyanoguanidine provide an increased yield of tobacco compared to untreated plants.

Although applicants do not want to be limited by theory, it is seen through experimentation that, as suggested by the preceding discussion, compounds of this invention are true plant-growth regulators, as measured by a number of criteria. Not only are they able to increase crop yields, they are also able to induce regulator effects in laboratory tests.

These effects fall into at least three classes of responses, all of which are consistent with the conclusion that these compounds represent a novel class of cytokinins. The observed responses include enhanced growth effects on translocation, as well as enhanced chlorophyll biosynthesis in some tissues with decreased chlorophyll degradation (senescence) in others. These responses suggest that the present class of compounds would be expected to elicit other known cytokinin plant tissue responses in addition to those described below and that a number of uses of these compounds pertaining to translocation of metabolites to storage organs or to temporary storage sites in the tissues or pertaining to delaying senescence and enhancing growth of certain plant tissues are implied from the mode of action of the compounds.

The compounds of the present invention have been found to substitute for a well-investigated cytokinin, $N^6$-benzyladenine, in promoting growth of cytokinin-dependent soybean callus in tissue culture. The cucumber cotyledon bioassay, described below, was used to define the compounds which possess cytokinin-like activity. As with many hormone-type bioassays, the response is log-linear with respect to concentration of compound required to elicit a response. The results the present compound had are two-fold, enhanced growth and enhanced rate of chlorophyll biosynthesis.

Growth promotive effects also were shown in two other systems as well. The growth of cotyledons could be stimulated in young, whole, radish seedlings with little effect on the growth of the rest of the seedling, that the length of the radicle may be reduced, and a more rapid enlargement is isolated leaf disks from lima bean could be effected.

Furthermore, the present compounds also direct the translocation of sucrose within the potato plant from one site to another. Whole potato plants receiving early hydroponic treatment with the present compounds were also found effective in early tuber development in that a greater proportion and weight of larger tubers were evident about half-way through tuber development.

Another property of the compounds was observed in senescence retardation of various plant systems. This was manifest by chlorophyll retention in tissues which were otherwise becoming yellow, indicating degrading of chlorophyll. This occurred with application to the foliage in spots or streaks (e.g., potato leaves), in leaf disks of cocklebur or of Romaine leaf lettuce, and in very young potato plants under adverse conditions.

The above-identified formula (V) guanidine compounds are highly effective for beneficially altering the growth and/or enhancing the yield of a wide variety of crops, such as:

Underground Stem Crops, including:
  Solanum tuberosum L.—white potato,
  Helianthus tuberosus—Jerusalem artichoke,
  Coloeasia antiguorum—Taro,
  Coloeasia esculenta—dasheen,
  Allium cepa—onion,
  Allium sativum—garlic,
  Allium porrum—leek,
  Allium schoenoprasum—chive, and
  Allium ascalowicum—shallot;
Underground Stem Ornamentals, including:
  Corms such as crocus or gladiolus,
  Bulbs such as tulips and hyacinths, and
  Rhizomes such as iris, canna or Solomon's seal;
Root Crops, including:
  Beta vulgaris—common beat, mangels and/or chard,
  Daucus carota—carrot,
  Tragopogon porrifolius—salsify,
  Pastinaca sativa—parsnip

*Raphanus sativus*—radish,
*Brassica rapa*—turnip
*Brassica napobrassica*—rutabaga,
*Ipomoea batatus*—sweet potato, yam,
*Pioscroa alata*—true yam,
*Manihot esculenta*—cassava, and
*Beta vulgaris*—sugar beet;
Graminaceous Crops, including:
  *Hordeum vulgare*—barley
  *Triticum aestivum*—wheat, and
  *Oryza sativa*—rice;
Cucurbits, including:
  *Cucumis sativus*, L.—cucumber, and
  *Cucurbita pepo*, L.—pumpkin
Fruit, including:
  *Pyrus malus* L.—apple;
Malvaceae, including:
  *Gossypium hirsutum*—cotton, and
  *Lycopersicon esculeutum*—tomatoes.

Surprisingly, it has also been found that certain of the formula (V) nitroguanidines and cyanoguanidines, for example, those in which $Y_5$ and $W_5$ are hydrogen; $Z_5$ and $X_5$ are halogen; and $R_4$, $R_5$, $R_6$, m, and n are as described above, are effective for increasing crop yields of rice (*Oryza sativa*), sunflowers (*Helianthus annus, L.*), alfalfa (*Medicago sativa*, L.), forage grasses (such as Agrostis spp., Bromus spp., Dactylis spp., and Pheleum spp.) and tobacco (*Nicotiana tobacum*, L.). When applied to tobacco plants prior to plant topping, and preferably when the plants are between about 5 cm and 140 cm in height, it has been found that the above-said nitroguanidines or cyanoguanidines retard senescence of the lower, more mature, tobacco leaves until younger leaves at the top of the treated plant are ready for harvest. This treatment represents a great advantage for the tobacco farmers because the number of pickings required for harvesting the crop are reduced. The tobacco from these treated plants is also more uniform than untreated tobacco.

These formula (V) compounds have the further advantage, when applied to rice or sunflowers, of increasing stem stiffness and/or stem diameter, thereby inhibiting the incidence of lodging of these crops.

Among the most effective compounds found to induce the above-mentioned desirable improvements in crops and crop yields are:

1-Nitro-3-($\alpha,\alpha,\alpha$-trifluoro-m-tolyl)guanidine;
1-(3,4-Dichlorophenyl)-3-nitroguanidine;
1-(m-Chlorophenyl)-3-nitroguanidine;
1-(3,5-Dichlorophenyl)-3-nitroguanidine;
1-(4-Chloro-$\alpha,\alpha,\alpha$-trifluoro-m-tolyl)-3-nitroguanidine;
1-Nitro-3-(3,5-xylyl)guanidine;
1-(4-Bromo-m-tolyl)-3-nitroguanidine;
1-Nitro-3-($\alpha,\alpha,\alpha$,4-tetrafluoro-m-tolyl)guanidine;
1-(3-Chloro-4-fluorophenyl)-3-nitroguanidine;
1-(m-Acetylphenyl)-3-nitroguanidine;
1-(m-Methoxybenzyl)-3-nitroguanidine;
1-(3,5-Dichlorophenyl)-1-methyl-3-nitroguanidine;
1-Cyano-3-($\alpha,\alpha,\alpha$,4-tetrafluoro-m-tolyl)guanidine;
1-(3-Chloro-4-fluorophenyl)-3-cyanoguanidine;
1-Cyano-3-(3,5-dichlorophenyl)guanidine;
1-(3-Chloro-4-hydroxyphenyl)-3-nitroguanidine;
1-(m-Methylbenzyl)-3-nitroguanidine;
1-Cyano-3-(m-methoxybenzyl)guanidine;
1-Nitro-3-veratrylguanidine;
1-(m-Fluorobenzyl)-3-nitroguanidine;
1-(p-Fluorobenzyl)-3-nitroguanidine;
1-(m-Bromophenyl)-3-nitroguanidine;
1-Nitro-3-(3,4,5-trichlorophenyl)guanidine;
1-(m-Bromophenyl)-3-cyanoguanidine;
1-Cyano-3-($\alpha,\alpha,\alpha$-trifluoro-m-tolyl)guanidine;
1-Benzyl-3-cyanoguanidine;
1-(m-Iodophenyl)-3-nitroguanidine;
1-Nitro-3-[m-(2,2,2-trifluoro-1,1-dihydroxyethyl)-phenyl]guanidine;
1-(4-Fluoro-m-tolyl)-3-nitroguanidine;
1-Nitro-3-(3,4-xylyl)guanidine;
1-($\alpha$-Methoxy-m-tolyl)-3-nitroguanidine;
1-Benzyl-3-nitroguanidine;
1-(4-Chloro-m-tolyl)-3-nitroguanidine;
1-[m-(Difluoromethoxy)phenyl]-3-nitroguanidine;
1-Nitro-3-(m-propoxybenzyl)guanidine;
1-($\alpha$-Methylbenzyl)-3-nitroguanidine;
1-(2-Fluoro-5-methylbenzyl)-3-nitroguanidine;
1-(2-Fluoro-5-methoxybenzyl)-3-nitroguanidine; and
1-Nitro-3-[m-(trifluoromethoxy)phenyl]guanidine.

Advantageously, the compounds of the present invention can be formulated as solid or liquid compositions which may be dispersed in a liquid or solid diluent for application to the foliage of plants or to the soil in which they are grown. The substituted guanidines of the invention may be formulated as flowable concentrates, emulsifiable concentrates, wettable powders, dusts, dust concentrates, and granular formulations.

A typical flowable liquid concentrate can be prepared by milling together, on a weight basis, about 46% of the substituted guanidine with about 0.4% colloidal magnesium aluminum silicate, about 1.5% naphthalene formaldehyde condensate, about 8% polyethylene glycol, about 0.1% nonylphenol ethylene oxide condensate (9–11 moles ethylene oxide), about 0.1% of a dispersing agent (i.e., sodium lignosulfonate), about 0.07% citric acid, about 46% water, and about 0.06% xanthan gum. This concentrate is dispersed in water for application as a liquid spray.

Another flowable liquid concentrate is prepared by admixing or milling together about 40%, by weight, of the substituted nitro or cyanoguanidine, about 0.40% colloidal magnesium aluminum silicate, about 1.50% sodium salts of polymerized alkyl naphthalene sulfonic acids, about 8.0% propylene glycol, about 0.1% ethoxylated octylphenol, about 0.1% nonylphenoxy polyethoxy ethanol, about 0.07% citric acid, about 0.06% xanthan gum, about 0.10% paraformaldehyde and about 49.77% water.

Emulsifiable concentrates can be prepared by dissolving, on a weight basis, about 10% of the active guanidine in about 38% of N-methylpyrrolidone, about 35% of a mixture of substituted benzenes, and about 10% of a spreader activator, having ingredients alkylarylpolyoxyethylene glycol, free-fatty acid and propanol, with about 7% by weight of a nonionic surfactant, such as octylphenoxy polyethoxy ethanol, nonylphenoxy polyethoxy ethanol, or the like. This concentrate is dispersed in water for application as a liquid spray. It may also be applied, undiluted to granular carriers, such as corncob grits, kaolin or attapulgite, to provide a granular formulation useful for application to soil in which any of the above-mentioned crops are grown.

Emulsifiable concentrates can also be prepared by dissolving, on a weight basis, about 11% of the active guanidine in about 57% of N-methylpyrrolidone, about 24% octyl alcohol, and about 8% polyoxyethylated castor oil.

A typical wettable powder can be prepared by grinding together, on a weight basis, about 20 to 45% of a finely-divided carrier (i.e., kaolin, bentonite, diatomaceous earth, attapulgite, or the like), about 45 to 80% of the active compound, about 2 to 5% of a dispersing agent (i.e., sodium lignosulfonate), and about 2 to 5% of a nonionic surfactant (i.e., octylphenoxy polyethoxy ethanol, nonylphenoxy polyethoxy ethanol, or the like). This formulation is generally dispersed in water for application as a liquid spray.

Advantageously, the guanidines of this invention may also be prepared as aqueous sprays or dips containing about 0.01 to 800.0 ppm of said guanidine. Said formulations are useful, as such, for treatment of harvested fruit, vegetables, and leafy ornamentals to inhibit their deterioration.

To facilitate understanding of the invention, the following nonlimitating examples are presented for the purpose of illustrating the present invention. Unless otherwise noted, all parts are by weight.

EXAMPLE 1

Preparation of 1-nitro-3-(3,4,5-trichlorophenyl)guanidine

To a slurry of N-methyl-N-nitroso-N'-nitroguanidine 3.3 g (0.0225 mol) in 200 ml of a 50% aqueous ethanol mixture is added 5.0 g (0.025 mol) of 3,4,5-trichloroaniline. This mixture is heated to 40° C. for 72 hours and then treated with one equivalent of NaOH to decompose excess N-methyl-N-nitroso-N'-nitroguanidine. The mixture is then filtered and acidified with concentrated HCl to give 1.6 g of a yellow solid which, when recrystallized, gives 1.4 g of the desired product. The melting point of the product is 209.5° C. dec.

The above procedure can be repeated except that the appropriate aniline is substituted for 3,4,5-trichloroaniline, and the period of heating is adjusted to yield the substituted nitroguanidines reported in Table I below. The reaction may be illustrated as follows:

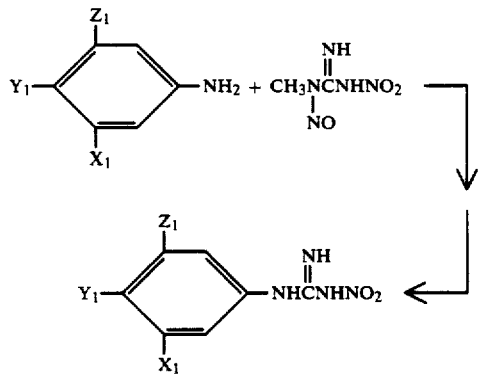

TABLE 1

| $X_1$ | $Y_1$ | $Z_1$ | Melting Point (°C.) |
|---|---|---|---|
| F | H | H | 172–174 |
| Cl | H | H | 162–163 |
| Br | H | H | 180–181 |
| I | H | H | 183–186 |
| $CF_3$ | H | H | 154.5–155.5 |
| $CH_3$ | H | H | 122–124 |
| $CH_2CN$ | H | H | 165–167 |
| $CH_2OCH_3$ | H | H | 106–107.5 |
| $CH_2OH$ | H | H | 138–140 |
| $COCH_3$ | H | H | 158–160 |
| $COCF_3.H_2O$ | H | H | 172–174 |
| $SCH_3$ | H | H | 155–157 |
| $OCHF_2$ | H | H | 122–124 |
| $OCF_3$ | H | H | 135–136.5 |
| $OCF_2CHF_2$ | H | H | 158–160 |
| $OCH_3$ | H | H | 151.5–153.5 |
| $OC_2H_5$ | H | H | 137.5–139 |
| CN | H | H | 207–208 |
| $NO_2$ | H | H | 194–196 |
| H | H | H | |
| $N(CH_3)_2$ | H | H | 158–159.5 |
| $COOCH_3$ | H | H | 173–175 |
| Cl | F | H | 171–173 |
| Cl | Cl | H | 155–156.5 |
| Cl | $CH_3$ | H | 176–177 |
| $CF_3$ | F | H | 168–170 |
| $CF_3$ | Cl | H | 212–213 |
| $CH_3$ | F | H | 182–183.5 |
| $CH_3$ | Br | H | 182–183 |
| $CH_3$ | Cl | H | 196.5–198 |
| $CH_3$ | $CH_3$ | H | 161–162.5 |
| Cl | H | Cl | 218–219 |
| Br | H | Br | 243 dec. |
| Br | H | $CH_3$ | 201–203 |
| $CH_3$ | H | $CH_3$ | 188–189 |
| $OCH_3$ | H | $CF_3$ | 152–154 |
| $CF_3$ | H | $CF_3$ | 224–226 |
| $OCH_3$ | H | $OCH_3$ | 208–209 |
| Cl | Cl | Cl | 210 dec. |
| COOH | H | H | 245–47 |
| $OC_6H_5$ | H | H | 138–39.5 |
| H | Br | H | 189–191 |
| H | $CF_3$ | H | 170–72 |
| H | $CH_2COOH$ | H | 199–200.5 |
| H | $OCF_2CHF_2$ | H | 152–53.5 |
| $NO_2$ | F | H | 171–72 |
| Cl | $CH_3O$ | H | 185.5–86.5 |
| $NH_2$ | $CH_3$ | H | 170.5–72.5 |
| $CH_3$ | $CH_3$ | $CH_3$ | 207–09 |

EXAMPLE 2

Preparation of 1-(3,5-dichlorophenyl)-2-methyl-3-nitroguanidine

PART A

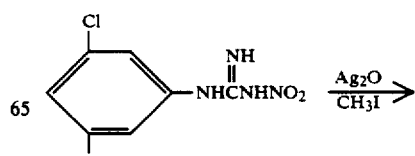

-continued
PART A

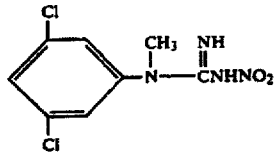

Methyl iodide (10 ml) is added to the nitroguanidine (2 g, 0.008 mol) and silver oxide (0.92 g, 0.004 mol), and the suspension refluxed. After two hours, the black suspension gradually becomes a yellow suspension. It is cooled to room temperature and filtered through diatomaceous earth. After concentration in vacuo, the crude product is recrystallized from ET$_2$O/THF to give 1.6 g (76%) of a white solid with melting point 136° C.–138° C. This procedure is also effective for preparing 1-methyl-3-nitro-1-(α,α,α,4-tetrafluoro-m-tolyl)guanidine, melting point 169° C.–171° C.

PART B

Preparation of
1-(4-Bromo-m-tolyl)-1-methyl-3-nitroguanidine

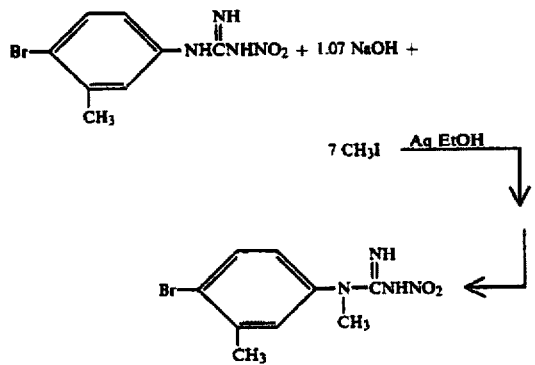

Sodium hydroxide (50% aq, 0.94 ml, 0.012 mol) is added in one portion to a homogeneous mixture of phenylnitroguanidine (3.00 g, 0.011 mol) and aqueous ethanol (5:1 ethanol:water, v/v). Methyl iodide (4.79 ml, 10.9 g, 0.077 mol) is added and the resultant mixture is stirred for 22 hours at 25° C. The white precipitate is filtered with water wash and recrystallized from ethanol to afford pure product (2.35 g, 74.6%, melting point 162° C.–164° C.).

PART C

Preparation of 1-benzyl-1-methyl-3-nitroguanidine

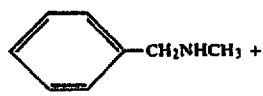

-continued

MNNG

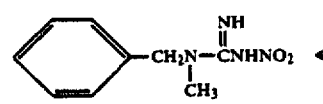

N-Methylbenzylamine (9.89 g, 0.082 mol) is added dropwise to a suspension of MNNG (10.0 g, 0.068 mol) in aqueous ethanol (1:1 ethanol:water, v/v) at 25° C. A gradual exotherm to 44° C. occurs over the next 15 minutes. After stirring for 42 hours at ambient temperature, the white slurry is filtered. The resultant white solid (7.13 g) is recrystallized from hexanes:ethanol to afford pure product (white crystals, 6.06 g, 43.0%, melting point 103° C.–107° C.).

EXAMPLE 3

Preparation of 1-(m-fluorobenzyl)-3-nitroguanidine

The compound m-fluorobenzylamine (7.5 g, 0.06 mol) is added to a slurry of N-methyl-N-nitroso-N'-nitroguanidine (8.33 g, 0.056 mol) in a 50% aqueous ethanol mixture. The thus-formed mixture is stirred for 18 hours, then treated with 1N NaOH (150 ml), and the mixture filtered. The filtrate is acidified with concentrated HCl, and the reaction mixture is then filtered to obtain the desired fluffy white solid product (10.6 g) having a melting point of 177° C.–179° C.

The above procedure is repeated using the appropriately substituted amine and 2-methyl-1(or 3)-nitro-2-thiopsuedourea to obtain the compounds illustrated in Table II below. The reaction is graphically illustrated as follows:

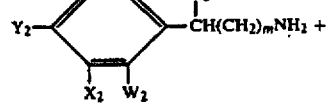

wherein m, $R_2$, $W_2$, $X_2$, $Y_2$, and $Z_2$ are as defined above.

TABLE II $$\text{structure: benzene ring with } Z_2, Y_2, X_2, W_2 \text{ substituents, and } CH(R_2)(CH_2)_m NHC(=NH)NHNO_2$$

| W₂ | X₂ | Y₂ | Z₂ | R₂ | m | Melting Point (°C.) |
|---|---|---|---|---|---|---|
| H | H | H | H | H | 0 | 179–180.5 |
| F | H | H | H | H | 0 | 181–183 |
| H | OH | H | H | H | 0 | 122–125 |
| H | OCH₃ | H | H | H | 0 | 134–136 |
| H | OC₂H₅ | H | H | H | 0 | 125–128 |
| H | OC₃H₇—n | H | H | H | 0 | 140.5–141.5 |
| H | OC₄H₉—sec | H | H | H | 0 | 93–98 |
| H | O-CH(OCH₂CH₂CH₂CH₂) (tetrahydropyranyloxy) | H | H | H | 0 | 110.5–113 |
| H | OCF₃ | H | H | H | 0 | 138–139 |
| H | SCH₃ | H | H | H | 0 | 149–152 |
| H | F | H | H | H | 0 | 177–179 |
| H | Cl | H | H | H | 0 | 166–167 |
| H | Br | H | H | H | 0 | 157–159 |
| H | I | H | H | H | 0 | 167–169 |
| H | CH₃ | H | H | H | 0 | 151–153 |
| H | C₂H₅ | H | H | H | 0 | 119–120.5 |
| H | CF₃ | H | H | H | 0 | 164–165 |
| H | H | F | H | H | 0 | 205–206 |
| H | H | Cl | H | H | 0 | 195–197 |
| H | H | Br | H | H | 0 | 172–174 |
| H | H | CH₃ | H | H | 0 | 181–183 |
| Cl | Cl | H | H | H | 0 | 220–222 |
| F | CH₃ | H | H | H | 0 | 198–198.5 |
| F | OCH₃ | H | H | H | 0 | 162–165 |
| Cl | H | Cl | H | H | 0 | 200–202 |
| F | H | F | H | H | 0 | 209–211 |
| F | H | H | CH₃ | H | 0 | 171.5–173 |
| F | H | F | H | H | 0 | 186–188 |
| F | H | H | OCH₃ | H | 0 | 149–151 |
| F | H | H | H | H | 1 | 153.5–154.5 |
| H | OCH₃ | H | H | H | 1 | 88–89 |
| H | OCH₃ | H | H | H | 2 | 122–123 |
| H | H | H | H | CH₃ | 0 | 115–116.5 |
| H | H | H | H | CF₃ | 0 | 149–151 |
| H | H | H | H | C₂H₅ | 0 | 129.5–130.5 |
| F | H | H | H | CH₃ | 0 | 99–102 |
| H | H | H | H | CH₃ | 0 | (+) isomer 126–127 |
| H | H | H | H | CH₃ | 0 | (−) isomer 127.5–128 |
| H | CH₃ | H | H | CH₃ | 0 | 140–143 |
| H | OCH₃ | H | H | CH₃ | 0 | 126–130 |
| H | H | F | H | CH₃ | 0 | 133–136 |
| Cl | H | H | H | H | 0 | 168–170 |
| OCH₃ | H | H | H | H | 0 | 202–205 |
| H | CN | H | H | H | 0 | 206 dec. |
| H | OC₆H₅ | H | H | H | 0 | 145–147 |
| H | COOCH₃ | H | H | H | 0 | 158–162 |
| H | CH₂CH₂COOC₂H₅ | H | H | H | 0 | 77–79 |
| H | OSO₂CH₃ | H | H | H | 0 | 134–137 |
| H | H | OCH₃ | H | H | 0 | 191.5–192.5 |
| H | H | N(CH₃)₂ | H | H | 0 | 211–213 |
| H | H | CH₂N(CH₃)₂ | H | H | 0 | 136–144 |
| H | H | CH₂NH₂ | H | H | 0 | 260° |
| H | H | CH₂CH₂COOC₂H₅ | H | H | 0 | 124–126 |
| H | H | CN | H | H | 0 | 166–168 |
| OCH₃ | H | OCH₃ | H | H | 0 | 200–201 |
| H | H | H | H | C₆H₅ | 0 | 236–237 |
| H | F | H | H | CH₃ | 0 | 135–138 |
| H | OCH₃ | OCH₃ | H | H | 0 | 152.5–153.5 |
| H | Cl | Cl | H | H | 0 | 208–210 |
| H | —O—CH₂—O— | | H | H | 0 | 207.5–209 |
| H | OCH₃ | H | OCH₃ | H | 0 | 166–168 |
| H | CH₃ | H | CH₃ | H | 0 | 178–180 |
| H | Cl | H | Cl | H | 0 | 218–219 |
| H | H | H | H | CH₃ | 1 | 178–180 |

TABLE II-continued

[Structure: Y₂, Z₂, X₂, W₂ substituted phenyl ring with —CH(CH₂)ₘNHCNHNO₂ group, R₂ substituent, and NH]

| W₂ | X₂ | Y₂ | Z₂ | R₂ | m | Melting Point (°C.) |
|---|---|---|---|---|---|---|
| H | H | H | H | CH₂C₆H₅ | 0 | 199.5–201 |
| OCH₃ | H | H | H | CH₃ | 0 | 188–192 |

EXAMPLE 4

Preparation of 1-cyano-3-(3,5-dichlorophenyl)guanidine

To a solution of 4.45 g (0.05 mol) of sodium dicyanamide in 50 ml of 1N HCl is added 8.1 g (0.05 mol) of 3,5-dichloroaniline in 50 ml of H₂O. The mixture is heated to about 80° C. to 100° C. for two hours. The mixture is then cooled, and the precipitated solids are recovered by filtration, washed and dried to give 8.75 g of the desired product having a melting point of 196° C.–198° C.

Following the above procedure, but substituting the appropriately substituted aniline for 3,5-dichloroaniline, provides the compounds reported in Table III below. The reaction may be graphically illustrated as follows:

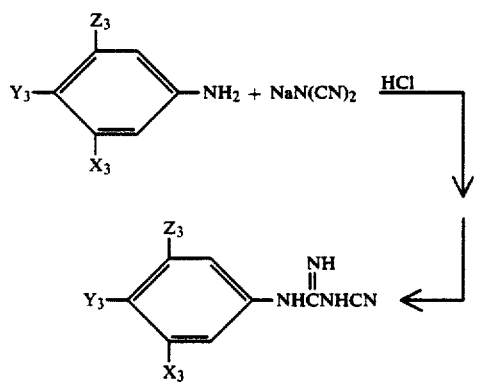

wherein X₃, Y₃, and Z₃ are as described above.

TABLE III

[Structure: Y₃, Z₃, X₃ substituted phenyl ring with —NHCNHCN group and NH]

| X₃ | Y₃ | Z₃ | Melting Point (°C.) |
|---|---|---|---|
| H | H | H | 195–196 |
| CF₃ | H | H | 203–206 |
| Cl | H | H |  |
| Br | H | H | 236–237 |
| NO₂ | H | H | 234–236 |
| OCH₃ | H | H | 182–184 |
| CH₃ | H | H |  |
| CN | H | H | 234–235.5 |
| Cl | OH | H |  |
| Cl | F | H | 214.5–216 |
| CF₃ | Cl | H | 194–196 |
| CF₃ | F | H | 146–148 |

TABLE III-continued

[Structure: Y₃, Z₃, X₃ substituted phenyl ring with —NHCNHCN group and NH]

| X₃ | Y₃ | Z₃ | Melting Point (°C.) |
|---|---|---|---|
| CH₃ | Br | H | 223–225 |
| Cl | CH₃ | H | 232–234 |
| Cl | Cl | H | 226–228 |
| Cl | H | Cl | 196–198 |
| COCH₃ | H | H | 175–178 |
| COOH | H | H |  |
| N(CH₃)₂ | H | H | 163.5–164.5 |
| COOCH₃ | H | H | 212–213 |
| H | Cl | H |  |
| H | OCH₃ | H |  |
| H | NHCOCH₃ | H |  |
| H | CH₃ | H |  |
| H | N(CH₃)₂ | H |  |
| H | OH | H |  |
| H | COOH | H |  |
| H | COCH₃ | H |  |
| H | N(C₂H₅)₂ | H |  |
| CH₃ | CH₃ | H |  |
| CH₃ | H | CH₃ | 224–227 |
| CF₃ | H | CF₃ | 263–265 |

Following the procedure of Example 4, but substituting the appropriately-substituted benzylamine for 3,5-dichloroaniline, provides the compounds reported in Table IV below. The reaction may be illustrated as follows:

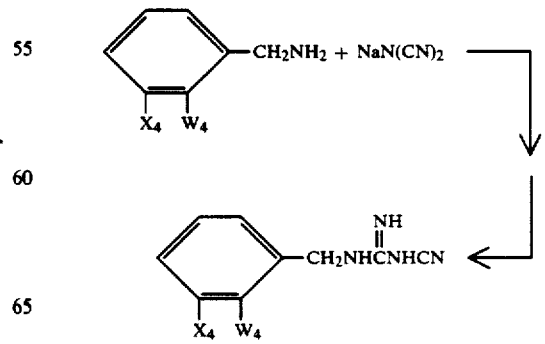

wherein W₄ and X₄ are as described above.

TABLE IV

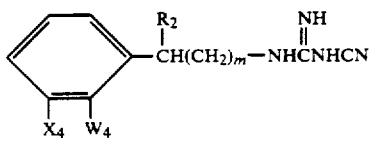

| W4 | m | X4 | Y4 | Z4 | R2 | Melting Point (°C.) |
|---|---|---|---|---|---|---|
| H | 0 | H | H | H | H | 100–101 |
| F | 0 | H | H | H | H | 129–130 |
| H | 0 | OCH3 | H | H | H | 112–114 |
| H | 0 | CH3 | H | H | H | 97–98.5 |
| H | 0 | F | H | H | H | 134–136 |
| H | 0 | H | Cl | H | H | 153–155 |
| H | 0 | H | F | H | H | 134–135 |
| F | 0 | H | H | CH3 | H | 123–124 |
| F | 0 | H | H | OCH3 | H | 129–131 |
| H | 0 | H | Cl | H | CH3 | 171–174 |
| H | 0 | H | H | H | CH3 | 156–158 |

EXAMPLE 5

Cucumber cotyledon greening bioassay for cytokinins

To evaluate test compounds for cytokinin stimulation in cucumber plants, plant cucumber seeds (National Pickling variety), placed in covered plastic trays, were soaked in moist vermiculite and were exposed to a green safelight. The trays were then placed in a dark environment for six days at 30° C.

Test solutions of compounds were prepared according to a 1 to 8 dilution series including 0.0156 ppm, 0.125 ppm, 1.0 ppm, 8 ppm, and 64 ppm of test compound. The solutions all contained 40 mM KCl, glass-distilled $H_2O$, and up to 1.25% acetone. (The compounds were initially dissolved in 100% acetone). Ten ml of diluted compound were placed in a 10 cm petri dish containing three layers of Whatman #1 cellulose filter papers. Again using dim green light, the cotyledons from the seedlings were excised using great care to discard the hook region, and eight pairs (16 cotyledons) were placed in each dish with the inner (upper) cotyledon surfaces downward. These were then incubated in the dark at 30° C. overnight (17 to 21 hours). These were placed in the dishes under fluorescent light, with an intensity of 12–14W per square meter, for a period of three hours. The dishes were kept at 20° C. or less in the dark while the cotyledons were sequentially collected and put into lots in large test tubes containing 5 ml of dimethylformamide. The tubes were sealed with Parafilm and placed at 4° C. in the dark, overnight, or at 30° C. in the dark for four hours to extract the chlorophyll.

The leachate was analyzed for absorbance at 663 nanometers (nm).

The cotyledons were removed and their surface areas were measured with a leaf-area meter. Data obtained with $N^6$-benzyladenine, a known cytokinin, were used to establish conditions for the test and to depict the cytokinin-like responses of the test compounds. Graphic curves were drawn to show (1) the increase in rate of chlorophyll biosynthesis (absorbance of leachate at 663 nm), and (2) the increase in cotyledon surface area (expansion). These data are presented FIGS. I and II. A compound of the present invention, 1-nitro-3-($\alpha,\alpha,\alpha$,4-tetrafluoro-m-tolyl)guanidine, is also evaluated in this test. A curve of the two responses obtained is compared with $N^6$-benzyladenine (a "Standard Cytokinin" against which other compounds can be compared). FIG. I reports greening data obtained in this test with the above-said compounds. FIG. II shows the expansion of the surface area of the cotyledon obtained with said compounds.*

The dose-response curves show that both $N^6$-benzyladenine and 1-nitro-3-($\alpha,\alpha,\alpha$,4-tetrafluoro-m-tolyl)-guanidine are active in this bioassay.

*These procedures are similar to those described by "Fletcher et al. 1982 Plant Physiology, 69: 675–677 and Moran and Porath. 1980 Plant Physiology."

FIG. I

Dose-response increase in rate of chlorophyll biosynthesis (absorbance of leachate at 663 nm) obtained with $N^6$-benzyladenine and a compound of the invention 1-nitro-3-($\alpha,\alpha,\alpha$,4-tetrafluoro-m-tolyl)-guanidine.

FIG. II

Dose-response increase in cotyledon surface area obtained with $N^6$-benzyladenine and 1-nitro-3-($\alpha,\alpha,\alpha$,4-tetrafluoro-m-tolyl)guanidine.

ANALOG TEST RESULTS-CUCUMBER COTYLEDON BIOASSAY

Compounds with moderate to excellent activity are listed below, along with the concentration of the compound, in parts per million, which is required to achieve 50% of the maximum response.

| CUCUMBER COTYLEDON BIOASSAY FOR CYTOKININS | |
|---|---|
| Compound | $ED_{50}$, PPM |
| 1-Nitro-3-($\alpha,\alpha,\alpha$,4-tetrafluoro-m-tolyl)guanidine | 0.48 |
| 1-(m-Methoxybenzyl)-3-nitroguanidine | 1.8 |
| 1-(3,5-Dichlorophenyl)-3-nitroguanidine | 0.125 |
| 1-Nitro-3-($\alpha,\alpha,\alpha$-trifluoro-m-tolyl)guanidine | 0.125 |
| 1-Cyano-3-($\alpha,\alpha,\alpha$-trifluoro-m-tolyl)guanidine | 0.22 |
| 1-Nitro-3-phenylguanidine | 8.0 |
| 1-Benzyl-3-nitroguanidine | 5.7 |
| 1-(m-Chlorobenzyl)-3-nitroguanidine | 3.8 |
| 1-Cyano-3-($\alpha,\alpha,\alpha$,4-tetrafluoro-m-tolyl)guanidine | 2.5 |
| 1-(m-Methoxyphenyl)-3-nitroguanidine | 1.0 |
| 1-(m-Iodophenyl)-3-nitroguanidine | 0.125 |
| 1-(m-Bromophenyl)-3-nitroguanidine | 0.48 |
| 1-(m-Bromophenyl)-3-cyanoguanidine | 1.0 |
| 1-(m-Chlorophenyl)-3-nitroguanidine | 1.8 |
| 1-(m-Chlorophenyl)-3-cyanoguanidine | 1.8 |
| 1-(m-Fluorophenyl)-3-nitroguanidine | 8.0 |
| 1-Nitro-3-m-tolylguanidine | 1.0 |
| 1-Cyano-3-m-tolylguanidine | 1.0 |
| 1-Cyano-3-($\alpha,\alpha,\alpha$-trifluoro-m-tolyl)guanidine | 0.22 |
| 1-(m-Methoxyphenyl)-3-nitroguanidine | 1.0 |
| 1-[m-Difluoromethoxy)phenyl]-3-nitroguanidine | 0.06 |
| 1-Nitro-3-[m-(trifluoromethoxy)phenyl]guanidine | 3.8 |
| 1-[m-(Methylthio)phenyl]-3-nitroguanidine | 1.0 |
| 1-(m-Ethoxyphenyl)-3-nitroguanidine | 3.8 |
| 1-Nitro-3-[m-(1,1,2,2-tetrafluoroethoxy)phenyl]guanidine | 0.48 |

CUCUMBER COTYLEDON BIOASSAY FOR CYTOKININS

| Compound | ED$_{50}$, PPM |
|---|---|
| 1-(α-Hydroxy-m-tolyl)-3-nitroguanidine | 2.5 |
| 1-(α-Methoxy-m-tolyl)-3-nitroguanidine | 1.8 |
| 1-Nitro-3-[m-(2,2,2-trifluoro-1,1-dihydroxyethyl)phenyl]guanidine | 0.48 |
| Methyl-m-(3-nitroguanidine)benzoate | 3.8 |
| 1-(m-Acetylphenyl)-3-nitroguanidine | 3.8 |
| 1-(m-Cyanophenyl)-3-nitroguanidine | 1.0 |
| 1-(m-Cyanophenyl)-3-cyanoguanidine | 8.0 |
| 1-[m-Cyanomethyl)phenyl]-3-nitroguanidine | 3.8 |
| 1-(m-Nitrophenyl)-3-nitroguanidine | 8.0 |
| 1-[m-Dimethylamino)phenyl]-3-nitroguanidine | 3.8 |
| 1-Cyano-3-(m-methoxyphenyl)guanidine | 2.5 |
| 1-(3-Chloro-4-fluorophenyl)-3-nitroguanidine | 1.8 |
| 1-(3-Chloro-4-fluorophenyl)-3-cyanoguanidine | 14.0 |
| 1-(3,4-Dichlorophenyl)-3-nitroguanidine | 1.0 |
| 1-(4-Bromo-m-tolyl)-3-nitroguanidine | 1.0 |
| 1-(4-Chloro-m-tolyl)-3-nitroguanidine | 1.8 |
| 1-(4-Fluoro-m-tolyl)-3-nitroguanidine | 3.8 |
| 1-Nitro-3-(3,4-xylyl)guanidine | 3.8 |
| 1-(4-Chloro-α,α,α-trifluoro-m-tolyl)-3-nitroguanidine | 1.0 |
| 1-(3,5-Dibromophenyl)-3-nitroguanidine | 0.125 |
| 1-(3,5-Dichlorophenyl)-3-nitroguanidine | 0.125 |
| 1-(3,5-Dichlorophenyl)-1-methyl-3-nitroguanidine | 3.8 |
| 1-Cyano-3-(3,5-dichlorophenyl)guanidine | 0.48 |
| 1-(3,5-Dimethoxyphenyl)-3-nitroguanidine | 14.0 |
| 1-(5-Bromo-m-tolyl)-3-nitroguanidine | 0.48 |
| 1-Nitro-3-(3,5-xylyl)guanidine | 3.8 |
| 1-(α,α,α,α',α'-Hexafluoro)-3,5-xylyl)-3-nitroguanidine | 3.8 |
| 1-(2-Fluoro-3-methoxybenzyl)-3-nitroguanidine | 2.5 |
| 1-Nitro-3-(3,4,5-trichlorophenyl)guanidine | 3.8 |
| 1-(4-Chloro-α,α,α-trifluoro-m-tolyl)-3-cyanoguanidine | 2.5 |
| 1-(o-Fluorobenzyl)-3-nitroguanidine | 3.8 |
| 1-(m-Iodobenzyl)-3-nitroguanidine | 14.0 |
| 1-(m-Chlorobenzyl)-3-nitroguanidine | 3.8 |
| 1-(m-Bromobenzyl)-3-nitroguanidine | 5.7 |
| 1-(m-Fluorobenzyl)-3-nitroguanidine | 8.0 |
| 1-(m-Methylbenzyl)-3-nitroguanidine | 8.0 |
| 1-Cyano-3-(m-methylbenzyl)guanidine | 8.0 |
| 1-(Nitro-3-[m-(trifluoromethyl)benzyl]guanidine | 8.0 |
| 1-(m-Methoxybenzyl)-3-nitroguanidine | 1.8 |
| 1-Cyano-3-(m-methoxybenzyl)guanidine | 2.5 |
| 1-(m-Hydroxybenzyl)-3-nitroguanidine | 1.0 |
| 1-(m-Ethoxybenzyl)-3-nitroguanidine | 8.0 |
| 1-Nitro-3-(m-propoxybenzyl)guanidine | 1.3 |
| 1-(m-sec-Butoxybenzyl)-3-nitroguanidine | 0.31 |
| 1-(p-Fluorobenzyl)-3-nitroguanidine | 8.0 |
| 1-Nitro-3-{m[(tetrahydro-2H—pyran-2-yl)oxy]benzyl}guanidine | 1.0 |
| 1-(2,5-Difluorobenzyl)-3-nitroguanidine | 5.7 |
| 1-(2-Fluoro-5-methoxybenzyl)-3-nitroguanidine | 2.5 |
| 1-(2-Fluoro-5-methylbenzyl)-3-nitroguanidine | 8.0 |
| 1-(2,4-Difluorobenzyl)-3-nitroguanidine | 10.6 |
| 1-(2,4-Dichlorobenzyl)-3-nitroguanidine | 8.0 |
| 1-(α-Methylbenzyl)-3-nitroguanidine | 1.8 |
| 1-(m-α-Dimethylbenzyl)-3-nitroguanidine | 14.0 |
| 1-(o-Fluorophenethyl)-3-nitroguanidine | 14.0 |
| 1-(m-Methoxyphenethyl)-3-nitroguanidine | 14.0 |
| 1-Nitro-3-[α-(trifluoromethyl)benzyl]guanidine | 2.5 |
| 1-(α-Ethylbenzyl)-3-nitroguanidine | 0.22 |

EXAMPLE 6

Tissue culture test to establish cytokinin mode of action

Cytokinins are involved with plant cell division. To specifically test for cytokinin-like activity of an unknown compound, said compounds must be able to substitute for a known cytokinin by allowing a cytokinin-dependent tissue culture to grow on a defined medium. Callus cultures derived from cotyledon tissue of soybeans (variety Acme) require a cytokinin in order to grow on agar media. These callus cultures are used in this evaluation to determine whether the compounds of the invention promote cell division.

Callus is prepared by subculturing on a basal medium containing vitamins, mineral salts, 3% sucrose, 0.9% agar, and naphthalene acetic acid at 2 ppm (PNAS 54: 1052–8 (1965)). The addition of $10^{-7}$M $N^6$-benzyladenine is normally required for callus to grow. Test media is prepared by omitting the known cytokinin ($N^6$-BA) and substituting test compounds at various concentrations. Four replicate dishes are used per test solution. Into 15×60 mm plastic Petri dishes is poured 6 ml of agar media containing test compounds. Callus is scraped from subculture plates, gently broken into small pieces and mixed with dilute agar in basal medium. Then, 2 ml of this is layered onto each test medium. After eight days at 25° C., in the dark, the dishes are examined for growth of the callus on the various test media. The data obtained are reported in Table IV below.

TABLE IV
GROWTH PROMOTION OF A CYTOKININ-DEPENDENT TISSUE CULTURE ON A DEFINED MEDIUM

| Compound | Concentration (PPM) | Percent of Callus[a] Which Is Growing |
|---|---|---|
| Untreated control | 0 | 0.3 |
| 1-(3,5-Dichloro-phenyl)-3-nitro-guanidine | 0.1 | 4.0 |
|  | 0.3 | 100.0 |
|  | 1.0 | 100.0 |
| 1-Nitro-3-(α,α,α,4-tetrafluoro-m-tolyl)-guanidine | 0.3 | 8.0 |
|  | 1.0 | 100.0 |
|  | 3.0 | 100.0 |
|  | 10.0 | 100.0 |
| 1-(m-Methoxybenzyl)-3-nitroguanidine | 3.0 | 15.0 |
|  | 10.0 | 100.0 |
|  | 30.0 | 100.0 |
|  | 100.0 | 100.0 |
| $N^6$—benzyladenine | $10^{-7}$ M | 100.0 |

[a]Growth is measured visually by comparing small brown cell clusters (not growing) to those which are large and white (growing).

It is seen that the compounds of the present invention do replace $N^6$-benzyladenine, thereby, indicating cytokinin-like activity.

EXAMPLE 7

Antisenescence properties on disks of leaf lettuce

Leaf disks are prepared from locally-purchased Romaine lettuce. The disks (4 per treatment) are placed in Petri dishes containing Whatman #1 filter papers and test solutions containing 10 ppm of test compound (with 0.2% acetone) or 100 ppm of test compound (with 2% acetone) in $H_2O$. After five days at room temperature in the dark, the disks are extracted with dimethylformamide, and absorbance of chlorophyll is measured at A 663 nm. Data obtained are reported in Table V.

TABLE V
ANTISENESCENCE PROPERTIES OF TEST COMPOUNDS APPLIED TO LEAF DISKS OF LEAF LETTUCE

| Treatment | Concentration (PPM) | Percent Increase In Chlorophyl Retention Over Untreated Controls |
|---|---|---|
| m-Trifluoromethyl-phenyldicyandiamide | 100 | 18 |
| 1-Benzyl-3-nitro-guanidine | 10 | 18 |
|  | 100 | 17 |
| 1-Nitro-3-(α,α,α-trifluoro-m-tolyl)guanidine | 100 | 16 |
| 1-(3,5-Dichlorophenyl)-3-nitroguanidine | 10 | 14 |
| 1-Nitro-3-(α,α,α,4-tetrafluoro-m-tolyl)guanidine | 10 | 40 |
| 1-(m-Methoxybenzyl)-3-nitroguanidine | 10 | 11 |
|  | 100 | 15 |
| 1-Cyano-3-(α,α,α,4-tetrafluoro-m-tolyl)guanidine | 10 | 33 |
|  | 100 | 17 |
| 1-(m-Methoxyphenyl)-3-nitroguanidine | 10 | 17 |
|  | 100 | 34 |
| 1-Cyano-3-(m-Methoxybenzyl)guanidine | 10 | 40 |
|  | 100 | 26 |
| 1-Nitro-3-[m-trifluoromethyl)benzyl]guanidine | 10 | 26 |
| 1-Nitro-3-phenylguanidine | 10 | 10 |

Lettuce leaf disks treated with the present compounds enhance chlorophyll retention about 10% to 40% over untreated controls.

EXAMPLE 8

Enlargement of leaf disks of lima bean

In this evaluation, lima bean leaf disks are found to respond to various compounds of this invention by increasing the growth of the disks when exposed to aqueous solutions of test compounds. Five or six leaf disks (combined area of 2.2 sq. cm) are placed in 15×100 mm Petri dishes with three layers of Whatman #1 filter paper and 12 ml of 40 mM KCl, plus various concentrations of test compounds. The dishes are kept in the light for six days, then disk area is measured with an area meter. Several of the test compounds are found to increase the amount of growth exhibited by the lima bean leaf disks. These data are reported in Table VI below.

TABLE VI
ENHANCED ENLARGEMENT OF LEAF DISKS OF LIMA BEANS

| Treatment | Concentration (PPM) | Percent Increase in Leaf Disk Area |
|---|---|---|
| Control | 0 | 54 |
| 1-(m-Methoxyphenyl)-3-nitroguanidine | 0.12 | 87 |
|  | 1.0 | 103 |
| 1-Nitro-3-(α,α,α,4-tetrafluoro-m-tolyl)-guanidine | 1.0 | 92 |
|  | 8.0 | 107 |

EXAMPLE 9

Determination of growth-promoting effects of nitroguanidines and cyanoguanidines on radish seedlings in liquid culture In this evaluation, surface-sterilized radish seeds, variety Cherry Belle, are asceptically placed in 125 ml Erlenmeyer flasks containing 20 ml autoclaved medium. The medium contains distilled water, mineral salts such as those used for plant tissue cultures (300 mg/l $KH_2PO_4$, 65 mg/l KCl, 4.9 mg/l $MnSO_4.H_2O$; 2.7 mg/l $ZnSO_4$; $7H_2O$; 1.8 mg/l $H_3BO_3$; 0.8 mg/l; 0.35 mg/l.$CuSo_4.5H_2O$; 0.1 mg/l $(NH_4)_6MO_7O_{24}.4H_2O$; 499 mg/l $Ca(NO_3)_2.O4H_2O$; 1 g/l $KNO_3$; 1 g/l $NH_4NO_3$; 71 mg/l $MgSO_4.7H_2O$; and 42 mg/l commercial 10% iron chelate), and an appropriate dilution of test compound prepared from a stock solution of 5000 ppm (technical compound) in acetone. The medium pH is adjusted to 5.8 before autoclaving, and the test compound is added after autoclaving of the medium, just prior to adding the 10 to 20 seeds per flask. Flasks are incubated on a reciprocating shaker for six days under dim fluorescent light at room temperature. At this time, seedlings are removed, blotted, and dissected into various organs which are weighed (fresh weight) and/or assessed for chlorophyll content.

Data obtained are reported in Table VII.

TABLE VII
GROWTH PROMOTING EFFECTS OF NITROGUANIDINES AND CYANOGUANIDINES ON RADISH SEEDLINGS

| Treatment | Concentration (PPM) | Percent Change In Fresh Weight of Radish Cotyledons Over Untreated Controls |
|---|---|---|
| Untreated controls | 0 | — |
| 1-(3,5-Dichloro-phenyl)-3-nitro-guanidine | 0.001 | −4 |
|  | 0.003 | −4 |
|  | 0.01 | +24 |
|  | 0.03 | +64 |
|  | 0.1 | +92 |
|  | 0.3 | +151 |

It can be seen that there is a 20% to 150% increase in radish cotyledon weights in comparison to untreated controls when 0.01 to 0.5 ppm 1-(3,5-dichlorophenyl)-3-nitroguanidine is used to treat said radish cotyledons.

EXAMPLE 10

Early increase in development of tubers of potato, Solanum tuberosum, variety Superior In greenhouse tests, young potato plants whose roots have been exposed to test compounds of the invention via hydroponic treatment for 48 hours have larger tubers early in tuber development than do untreated plants. This suggests that under field conditions, treated plants could produce more tubers that would reach the status of U.S. No. 1's.

In these tests, potato plants, variety Superior, are grown in vermiculite until they are 7 cm tall. They are then treated hydroponically with aqueous solutions of test compound at various concentrations for 48 hours. Thereafter, the potato plants are planted in greenhouse soil and grown for two months before evaluation. Four plants are used per treatment. In plants treated with test compounds, more tubers with weights above 2 oz. are in evidence early in tuber development. In untreated plants, 20% (w/w) of the young tubers are in this weight class while in treated plants, 29 to 81% (w/w) of the tubers are in this class. For perspective, the tubers weighing over 2 oz. have probably reached 40 to 60% of their expected weight, were they to become U.S. #1's.

Data obtained are reported in Table VIII below.

TABLE VIII

EARLY INCREASE IN SIZE OF DEVELOPING TUBERS OF POTATO, VARIETY SUPERIOR

| | | Tubers Weighing Over 2 oz. (55 g) | | |
|---|---|---|---|---|
| Treatment | Concentration (PPM) | Total Weight (g) | Percent Increase Over Untreated Controls | Percent of Total Tuber Weight |
| Untreated control | 0 | 77 | 0 | 20 |
| 1-(3,5-Dichlorophenyl)-3-nitroguanidine | 0.1 | 175 | 127 | 52 |
| | 1.0 | 240 | 217 | 57 |
| 1-Nitro-3-(α,α,α-trifluoro-m-tolyl)guanidine | 0.1 | 102 | 32 | 29 |
| | 1.0 | 140 | 82 | 41 |
| | 10.0 | 419 | 184 | 81 |
| 1-(m-Methoxybenzyl)-3-nitroguanidine | 1.0 | 107 | 39 | 32 |
| | 10.0 | 108 | 40 | 29 |
| | 100.0 | 182 | 136 | 64 |

EXAMPLE 11

Evaluation of test compounds for inhibiting lodging of paddy rice

In this evaluation, IR-36 paddy rice is transplanted into 12 m² plots in four replicates at the rate of three seedlings per hill. Hill spacing is 25×25 cm. A basal application of fertilizer N,P,K at 60, 40, and 40 kg/ha is made and followed by an additional application of nitrogen (30 kg/ha) 30 and 50 days after the plots are sprayed with an aqueous-acetone mixture (20/80) of test compound containing 0.25% of a nonionic wetting agent (i.e., nonylphenol containing 9 mols of ethylene oxide, oleic acid, and isopropanol). Application of test compound is made at the panicle development stage approximately equivalent to Zadok's stage Z31/32. These evaluations are conducted in an area where lodging pressure is normally severe. During the growing season, water is maintained in the paddies at a depth of about 3 to 5 cm. Four months after transplanting, the plots are examined, and the rice harvested from 6 m² sampling areas. Data obtained are reported below.

| Treatment | Concentration kg/ha | Percent Lodging |
|---|---|---|
| Untreated control | 0 | 100 |
| 1-(3,5-Dichlorophenyl)-3-nitroguanidine | 1 | 20 |
| | 2 | 10 |
| | 4 | 5 |

EXAMPLE 12

Evaluation of test compounds for increasing yield in paddy rice

The procedure of Example 11 is repeated except that the aqueous-acetone mixture containing test compound is applied to transplanted IR-36 paddy rice when it reaches the maximum tillering stage. Also, the aqueous-acetone (20/80) mixture containing test compound and nonionic wetting agent is applied to the tillered rice at rates sufficient to provide 11, 33, or 100 g/ha of test compound. About four months after transplanting, the rice is harvested, with the resultant data reported below.

| RICE YIELD ENHANCEMENT | | | |
|---|---|---|---|
| Treatment | Rate g/ha | Yield,* Ton/ha | Yield Percent of Control |
| Untreated control | — | 4.46 | 100 |
| 1-Potassium-3-(3,5-dichlorophenyl)-1-nitroguanidine | 11 | 5.21 | 117 |
| | 33 | 4.70 | 105 |
| | 100 | 4.58 | 103 |

*at 14% moisture

EXAMPLE 13

Evaluation of test compounds for increasing grain yield in wheat and barley

Surprisingly, it is also noted that these compounds are effective for inducing early maturation of grains such as wheat and barley.

During the third week of May, fields previously plowed, harrowed, and fertilized with 896 kilograms/hectare of a 9:9:9 chemical fertilizer are seeded in one section with 2.44 hectoliters/hectare of Spring wheat (variety Sinton).

In another section, the field is seeded with 2.09 hectoliters/hectare of Spring barley (variety Herta). Each field is staked out in 12 square meter plots. When the plants reach the Z30/Z31 Zodak's stage, the plots are then sprayed with an 80:20 acetone/water mixture containing 0.25% of a nonionic wetting agent (i.e., nonylphenol containing 9 mols of ethylene oxide, oleic acid, and isopropanol) and a sufficient amount of test compound to provide 0 (untreated control), 0.22, 0.67, or 2.0 ka/ha of said test compound. Each treatment is replicated five times. Seven weeks after planting, the plots are harvested. The harvested grain is then normalized to 15% moisture content and weighed. Data obtained are reported in Table IX below.

TABLE IX

EVALUATION OF TEST COMPOUNDS FOR INCREASING GRAIN YIELD IN WHEAT AND BARLEY

| Compound | Crop | Rate Kg/Ha | Grain Yield Hectoliters/Hectare | Percent of Control |
|---|---|---|---|---|
| 1-(3,5-Dichlorophenyl)- | Spring | 0 (control) | 25.84 | — |
| 3-nitroguanidine | Wheat | 0.22 | 29.84 | 115 |
|  |  | 0.67 | 30.80 | 119 |
|  |  | 2.0 | 29.32 | 113 |
| 1-(3,5-Dichlorophenyl)- | Spring | 0 (control) | 22.62 | — |
| 2-methyl-3-nitro- | Wheat | 0.22 | 25.14 | 111 |
| guanidine |  | 0.67 | 26.19 | 116 |
|  |  | 2.0 | 24.80 | 110 |
| 1-(3,5-Dichlorophenyl)- | Spring | 0 (control) | 30.10 | — |
| 3-nitroguanidine | Barley | 0.22 | 32.90 | 108 |
|  |  | 0.67 | 33.20 | 109 |
|  |  | 2.0 | 34.80 | 114 |

EXAMPLE 14

Evaluation of test compounds as yield-enhancing agents for cotton (*Gossypium hirsutum* cv Acala)

In this evaluation, a field, previously plowed, harrowed, and fertilized, is seeded with cotton (*Gossypium hirsutum* cv Acala) during the third week of April. Plantings are made to provide approximately one meter spacing between rows and an average of about 12 plants per meter. Each plot is four meters in length, and three replicates per treatment are used. Four weeks after planting, when the cotton plants have reached the two- to three-leaf stage, the plants are sprayed with a 50:50 acetone/water mixture containing 0.25% of a nonionic, modified phthalic glycerol alkyl resin, emulsifier-spreader, and a sufficient amount of test compound to provide 0.0 (untreated control), 0.062, 0.125, or 0.25 kg/ha of test compound. About seven weeks after planting, when the cotton plants have reached the stage of first flowering, different plots (previously untreated), but in the same field, are sprayed with solutions of test compound prepared as described above. All plants are then permitted to grow to maturity using normal cultural practices. During the second week of October, the cotton from each plot is hand harvested, and the weight of the seed cotton determined for each plot. The results obtained from all treatments are reported in Tables X and XI below as the average weight in kg/ha of seed cotton obtained from the three replicates of each treatment.

TABLE X

EVALUATION OF 1-NITRO-3-(α,α,α,4-TETRAFLUORO-m-TOLYL)GUANIDINE FOR YIELD ENHANCEMENT OF COTTON

| Time of Application | Rate kg/ha | Average Yield of Seed Cotton (kg)/Plot |
|---|---|---|
| 2–3 leaf | 0.0 (control) | 1.57 |
|  | 0.062 | 1.72 |
| 2–3 leaf | 0.0 (control) | 1.70 |
|  | 0.125 | 1.85 |
| 2–3 leaf | 0.0 (control) | 1.97 |
|  | 0.25 | 2.22 |
| First flowering | 0.0 (control) | 1.73 |
|  | 0.062 | 2.25 |
| First flowering | 0.0 (control) | 1.61 |
|  | 0.125 | 2.20 |
| First flowering | 0.0 (control) | 1.85 |
|  | 0.25 | 2.45 |

EXAMPLE 15

Evaluation of test compounds to determine their efficacy for increasing the number of U.S. No. 1 potatoes and the total weight of potatoes produced per plant In this evaluation, white potatoes (*Solanum tuberosum* Superior) (2016 kg/ha) are planted during the first week of April. Approximately five weeks after planting, when more than 80% of the potato plants have emerged, plots comprising two 9.6 miter rows, spaced 0.9 meters apart, are sprayed with a 50:50 acetone/water mixture containing 0.25% by weight of a modified phthalic glycerol alkyl resin, nonionic emulsifier-spreader, and sufficient test compound to provide 0.0 (untreated control), 0.25, 0.50 or 1.0 kg/ha of test compound. Six replicates per treatment are used. At one-week intervals, additional plots are sprayed in the same manner and at the same rates as described above.

The treated plants are cared for in accordance with normal cultural practices utilized in the growing of potatoes. When said plants reach maturity, about 20 weeks after planting, they are harvested. The total number of U.S. No. 1 potatoes per plot and total weight of all potatoes per plot are determined. Data obtained are reported in Tables XI and XII below.

TABLE XI

EVALUATION OF TEST COMPOUNDS FOR INCREASING THE NUMBER OF U. S. NO. 1 POTATOES PER PLANT USING WHITE POTATOES (*SOLANUM TUBEROSUM* CV. SUPERIOR)

| Compound | Rate kg/ha | % (±) Untreated Control of U. S. No. 1 Potatoes | | |
|---|---|---|---|---|
| | | E1 | E2 | E3 |
| 1-Nitro-3-(α,α,α,4-tetrafluoro m-tolyl)guanidine | 1.0 | +21 | +27 | +15 |
| | 0.50 | +23 | +28 | +14 |
| | 0.25 | +21 | +30 | +19 |
| 1-(3-Chloro-4-fluorophenyl)-3-nitroguanidine | 1.0 | +19 | +24 | +19 |
| | 0.50 | +25 | +20 | +7 |
| | 0.25 | +21 | +24 | +14 |
| 1-(m-Methoxybenzyl)-3-nitroguanidine | 1.0 | +10 | +36 | +19 |
| | 0.50 | +18 | +32 | +20 |
| | 0.25 | +23 | +34 | +18 |
| 1-(3,5-Dichlorophenyl-3-nitroguanidine | 1.0 | +12 | +38 | +13 |
| | 0.50 | +14 | +35 | +8 |
| | 0.25 | +15 | +34 | +10 |

E1, E2, E3 = Application of test compound one, two, or three weeks after plant emergence of the potato plants.
(±) = Increase or decrease over untreated controls.

TABLE XII

EVALUATION OF TEST COMPOUNDS FOR INCREASING THE TOTAL WEIGHT OF POTATOES (*SOLANUM TUBEROSUM* SUPERIOR) [WHITE POTATOES] COMPARED TO UNTREATED CONTROLS YIELDING 188 POUND/PLOT (380 CWT/ACRE, 42.6 METRIC TONS/HA) OF SAID POTATOES

| Compound | Rate kg/ha | Total Potato Yield Per Treatment % (±) Untreated Control | | |
|---|---|---|---|---|
| | | E1 | E2 | E3 |
| 1-Nitro-3-(α,α,α,4-tetrafluoro-m-tolyl)nitroguanidine | 1.0 | +17 | +23 | +13 |
| | 0.50 | +19 | +24 | +12 |
| | 0.25 | +18 | +26 | +16 |
| 1-(3-Chloro-4-fluorophenyl)-3-nitroguanidine | 1.0 | +15 | +20 | +17 |
| | 0.50 | +21 | +16 | +5 |
| | 0.25 | +18 | +20 | +11 |
| 1-(m-Methoxybenzyl)-3-nitroguanidine | 1.0 | +7 | +25 | +16 |
| | 0.50 | +15 | +38 | +17 |
| | 0.25 | +20 | +30 | +14 |
| 1-(3,5-Dichlorophenyl)-3-nitroguanidine | 1.0 | +11 | +32 | +11 |
| | 0.50 | +12 | +30 | +6 |
| | 0.25 | +9 | +28 | +7 |

E1, E2, and E3 indicate the time of application of test compound one, two, or three weeks, respectively, after emergence of the potato plants.
(±) = Increase or decrease over untreated controls.

EXAMPLE 16

Evaluation of test compounds to determine their efficacy for increasing the total weight of potatoes produced The procedure of Example 15 is repeated except that a variety of compounds is evaluated. The compounds are applied two weeks after the seedling plants have emerged, at application rates from 0.25 kg/ha to 2.0 kg/ha. The potatoes are harvested about 20 weeks after planting, and data obtained are reported in Table XIII below where the total fresh weight of potatoes from treated plots is compared with the total fresh weight of potatoes obtained from untreated plots. The same procedure as described above is employed except that the test compounds are prepared as a 30% liquid flowable formulation which is dispersed in water and applied as an aqueous spray. Data obtained with these flowable formulations is reported in Table XIII-A.

The flowable concentrates used in this evaluation comprise:

| | Percent W/W |
|---|---|
| Test compound (90% pure) | 30.00 |
| Colloidal magnesium aluminum silicate | 0.40 |
| Sodium salts of polymerized alkyl | 1.50 |

-continued

| | Percent W/W |
|---|---|
| naphthalene sulfonic acids | |
| Propylene glycol/dipropylene glycol | 8.00 |
| Ethoxylated octylphenol | 0.10 |
| Nonylphenoxy polyethoxyethanol | 0.10 |
| Citric acid | 0.07 |
| Xanthan gum | 0.06 |
| Paraformaldehyde | 0.10 |
| Tap water | 59.67 |
| | 100.00 |

TABLE XIII

EVALUATION OF TEST COMPOUNDS TO DETERMINE THEIR EFFICACY FOR INCREASING THE TOTAL WEIGHT OF POTATOES PRODUCED

| Treatment | Rate kg/ha | Total Tuber Fresh Weight Percent (±) Untreated Controls |
|---|---|---|
| Untreated controls | — | 151 cwt/A* |
| 1-Benzyl-3-nitroguanidine | 2.0 | +12 |
| | 0.5 | +13 |
| 1-Nitro-3-(α,α,α-trifluoro-m-tolyl)guanidine | 0.5 | +9 |
| 1-(m-acetylphenyl)-3-nitroguanidine | 1.0 | +18 |
| | 0.25 | +6 |
| 1-(m-Methoxyphenethyl)-3-nitroguanidine | 2.0 | +5 |
| | 0.5 | +10 |

TABLE XIII-continued

EVALUATION OF TEST COMPOUNDS TO DETERMINE THEIR EFFICACY FOR INCREASING THE TOTAL WEIGHT OF POTATOES PRODUCED

| Treatment | Rate kg/ha | Total Tuber Fresh Weight Percent (±) Untreated Controls |
|---|---|---|
| 1-(4-Chloro-m-tolyl)-3-nitroguanidine | 0.5 | +4 |
| 1-(m-Methoxyphenyl)-3-nitroguanidine | 0.5 | +3 |
| 1-(m-Fluorobenzyl)-3-nitroguanidine | 2.0 | +6 |
| 1-(m-Bromophenyl)-3-nitroguanidine | 2.0 | +2 |
|  | 0.5 | +17 |
| 1-Nitro-3-(3,4-xylyl)guanidine | 0.5 | +3 |
| 1-[m-(Difluoromethoxy)phenyl]-3-nitroguanidine | 2.0 | +2 |
|  | 0.5 | +20 |
| 1-Nitro-3-(m-propoxybenzyl)guanidine | 2.0 | +25 |
| 1-(α-Methylbenzyl)-3-nitroguanidine | 2.0 | +9 |
|  | 0.5 | +16 |

*Cwt/A = Hundred weight per acre

TABLE XIII-A

EVALUATION OF TEST COMPOUNDS FORMULATED AS FLOWABLE CONCENTRATES TO DETERMINE THEIR EFFICACY FOR INCREASING THE TOTAL WEIGHT OF POTATOES PRODUCED

| Treatment | Rate kg/ha | Total Tuber Fresh Weight Percent (±) Untreated Controls |
|---|---|---|
| 1-Nitro-3-(α,α,α-trifluoro-m-tolyl)guanidine | 0.5 | +11 |
|  | 0.25 | +11 |
|  | 0.125 | +11 |
| 1-(3,5-Dichlorophenyl)-3-nitroguanidine | 0.5 | +8 |
|  | 0.25 | +8 |
|  | 0.125 | +11 |
| 1-Nitro-3-(α,α,α,4-tetrafluoro-m-tolyl)guanidine | 0.5 | +8 |
|  | 0.25 | +8 |
|  | 0.125 | +4 |
| 1-(m-Methoxybenzyl)-3-nitroguanidine | 0.5 | +6 |
|  | 0.25 | +13 |
|  | 0.125 | +5 |

Untreated control average total yield 202 cwt/A.

EXAMPLE 17

Evaluation of test compounds to determine their efficacy for increasing the total weight of Kennebec variety potatoes produced The procedure of Example 15 is again repeated except that Kennebec variety potatoes are used for the evaluations. Test compounds are applied as aqueous-/acetone mixtures per Example 15 but at rates sufficient to provide from 0.5 kg/ha to 2.0 kg/ha. The potatoes are harvested at maturity, about 20 weeks after planting, and data obtained are reported in Table XIV. Data are reported as total fresh weight of potatoes compared with the total fresh weight of potatoes obtained from untreated controls.

TABLE XIV

EVALUATION OF TEST COMPOUNDS TO DETERMINE THEIR EFFICACY FOR INCREASING THE TOTAL WEIGHT OF KENNEBEC VARIETY POTATOES

| Treatment | Rate kg/ha | Total Tuber Fresh Weight Percent (±) Untreated Controls |
|---|---|---|
| 1-Cyano-3-(α,α,α-trifluoro-m-tolyl)guanidine | 2.0 | +14 |
|  | 0.5 | +7 |
| 1-Benzyl-3-cyanoguanidine | 0.5 | +16 |
| 1-(m-Chlorophenyl)-3-nitroguanidine | 2.0 | +9 |
| 1-Nitro-3-(3,5-xylyl)guanidine | 2.0 | +9 |
| 1-(m-Methoxybenzyl)-3-nitroguanidine | 2.0 | +15 |
|  | 0.5 | +6 |
| 1-(m-Methylbenzyl)-3-nitroguanidine | 2.0 | +6 |
| 1-Cyano-3-(m-Methoxybenzyl)guanidine | 2.0 | +5 |
| 1-(p-Fluorobenzyl)-3-nitroguanidine | 2.0 | +8 |
|  | 0.5 | +4 |

EXAMPLE 18

Evaluation of test compounds for increasing total potato yield and increasing production of U.S. No. 1 potatoes on different potato varieties The procedure of Example 15 is employed with the following exceptions: (1) test compounds are applied at two rates, 0.25 and 1.0 kg/ha, (2) several different varieties of white potatoes (Solanum tuberosum) are used, and (3) the compounds are applied one or two weeks after the potato plants have emerged from the soil. The several varieties of potatoes employed in this evaluation are Katahdin, Kennebec, Norchip, and Superior.

Data obtained are reported in Table XV below.

TABLE XV

EVALUATION OF TEST COMPOUNDS FOR INCREASING THE TOTAL WEIGHT OF POTATOES AND THE NUMBER OF U.S. NO. 1 POTATOES PRODUCED PER PLANT

| Compound | Rate kg/ha | VARIETY KATAHDIN Tuber Fresh Weight % (±) Untreated Controls | | | |
|---|---|---|---|---|---|
| | | E 1 | | E 2 | |
| | | U.S. No. 1 | Total | U.S. No. 1 | Total |
| 1-Nitro-3-(α,α,α,4-tetrafluoro-m-tolyl)guanidine | 1.0 | +13 | +14 | +12 | +15 |
|  | 0.25 | +13 | +12 | +15 | +18 |
| 1-(m-Methoxybenzyl)-3-nitroguanidine | 1.0 | +21 | +21 | +11 | +13 |
|  | 0.25 | +18 | +18 | +4 | +6 |
| Untreated controls: Average yield - 207 cwt/A, U.S. No. 1; 232 cwt/A total. | | | | | |
| 1-Nitro-3-(α,α,α,4-tetrafluoro-m-tolyl)nitroguanidine | 1.0 | −11 | −8 | +16 | +17 |
|  | 0.25 | +6 | +5 | +9 | +10 |
| 1-(m-Methoxybenzyl)-3-nitroguanidine | 1.0 | −3 | −2 | +3 | +4 |
|  | 0.25 | 0 | +1 | +4 | +6 |
| Untreated controls: Average yield - 257 cwt/A, U.S. No. 1; 307 cwt/A total. | | | | | |
| 1-Nitro-3-(α,α,α,4-tetrafluoro-m-tolyl)guanidine | 1.0 | +12 | +11 | +1 | +4 |
|  | 0.25 | +7 | +7 | +7 | +7 |

TABLE XV-continued
EVALUATION OF TEST COMPOUNDS FOR INCREASING THE TOTAL WEIGHT OF POTATOES AND THE NUMBER OF U.S. NO. 1 POTATOES PRODUCED PER PLANT

| | | VARIETY KATAHDIN | | | |
|---|---|---|---|---|---|
| | | Tuber Fresh Weight % (±) Untreated Controls | | | |
| | Rate | E 1 | | E 2 | |
| Compound | kg/ha | U.S. No. 1 | Total | U.S. No. 1 | Total |
| 1-(m-Methoxybenzyl)-3- | 1.0 | +7 | +7 | +3 | +5 |
| nitroguanidine | 0.25 | +10 | +10 | +4 | +3 |
| Untreated controls: Average yield - 302 cwt/A, U.S. No. 1; 368 cwt/A total. | | | | | |
| 1-Nitro-3-(α,α,α,4-tetra- | 1.0 | +16 | +14 | +19 | +19 |
| fluoro-m-tolyl)guanidine | 0.25 | +14 | +14 | +22 | +21 |
| 1-(m-Methoxybenzyl)-3- | 1.0 | +14 | +13 | +16 | +14 |
| nitroguanidine | 0.25 | +17 | +15 | +27 | +22 |
| Untreated controls: Average yield 283 cwt/A, U.S. No. 1; 322 cwt/A, total | | | | | |

E 1 = Test compound applied one week after emergence of potato plants.
E 2 = Test compound applied two weeks after emergence of potato plants.
Cwt/A = Hundred weight per acre.
(±) = Increase or decrease over untreated controls.

EXAMPLE 19

Evaluation of test compounds for increasing total fresh weight of potatoes (*Solanum tuberosum* Superior)

The procedure of Example 15 is repeated except that a variety of compounds is evaluated at rates of from 0.125 kg/ha to 1.0 kg/ha, and the 50/50 aqueous/acetone mixture containing 0.25% of the nonionic surfactant and the test compound is applied to the potato plants three weeks after they have emerged from the soil.

The potatoes are harvested about 20 weeks after planting, and the total weight of potatoes from treated plants is compared to the total weight of potatoes from the untreated controls. Data obtained are reported in Table XVI below.

TABLE XVI
EVALUATION OF TEST COMPOUNDS APPLIED THREE WEEKS AFTER EMERGENCE OF THE POTATO PLANTS (VARIETY SUPERIOR)

| Compound | Rate kg/ha | Total Tuber Fresh Weight % (±) Untreated Controls |
|---|---|---|
| 1-Benzyl-3- | 1.0 | +9 |
| nitroguanidine | 0.5 | +8 |
| | 0.25 | +5 |
| | 0.125 | +2 |
| Untreated controls average total yield: 402 cwt/A | | |
| 1-Nitro-3-(α,α,α- | 1.0 | +11 |
| trifluoro-m-tolyl)- | 0.5 | +15 |
| guanidine | 0.25 | +9 |
| | 0.125 | +1 |
| Untreated controls average total yield: 389 cwt/A | | |
| 1-Cyano-3-(α,α,α- | 1.0 | +7 |
| trifluoro-m-tolyl)- | 0.5 | +2 |
| guanidine | 0.25 | −5 |
| | 0.125 | −4 |
| Untreated controls average total yield: 398 cwt/A | | |
| 1-(m-chlorophenyl)- | 1.0 | +10 |
| 3-nitroguanidine | 0.5 | +6 |
| | 0.25 | +3 |
| | 0.125 | +7 |
| 1-(4-Chloro-α,α,α- | 1.0 | +10 |
| trifluoro-m-tolyl)- | 0.5 | +5 |
| 3-nitroguanidine | 0.25 | +8 |
| | 0.125 | +4 |
| Untreated controls average total yield: 391 cwt/A | | |
| 1-(4-Bromo-m-tolyl)- | 1.0 | +2 |
| 3-nitroguanidine | 0.5 | +4 |
| | 0.25 | +4 |
| | 0.125 | +6 |
| Untreated controls average total yield: 410 cwt/A | | |
| 1-(3-Chloro-4- | 1.0 | +8 |
| fluorophenyl)-3- | 0.5 | +6 |
| nitroguanidine | 0.25 | +5 |
| | 0.125 | 0 |
| Untreated controls average total yield: 412 cwt/A | | |

Cwt/A = Hundred Weight/Acre.
(±) = Increase or decrease over untreated controls.

EXAMPLE 20

Evaluation of test compounds for increasing the total potato yield and the number of U.S. No. 1 potatoes per plant using white potatoes (*Solanum tuberosum* Superior)

The procedures of Example 15 is repeated except that test compounds are applied at rates of from 0.0625 kg/ha to 1.0 kg/ha three weeks after planting, two weeks pre-emergence or three weeks post-emergence. The test compounds are applied in 50/50 aqueous/acetone mixture containing 0.25% of the nonionic surfactant and sufficient test compound to provide for 0.0625 kg/ha to 1.0 kg/ha. The potatoes are harvested when they reach maturity, about 20 weeks after planting.

Data obtained are reported in Table XVII below.

TABLE XVII
EVALUATION OF TEST COMPOUND FOR INCREASING THE TOTAL WEIGHT OF POTATOES AND THE NUMBER OF U.S. NO. 1 POTATOES PRODUCED PER PLANT WHEN THE TEST COMPOUND IS APPLIED THREE WEEKS POST PLANTING - TWO WEEKS PRE-EMERGENCE

| | Rate | Tuber Fresh Weight % (±) Untreated Controls | |
|---|---|---|---|
| Compound | kg/ha | U.S. No. 1 | Total |
| 1-(3-5-Dichlorophenyl)-3-nitroguanidine | 1.0 | +13 | +14 |
| Untreated controls average yield: | 0.5 | +7 | +8 |
| 364 cwt/A U.S. No. 1, 394 cwt/A total | 0.25 | +4 | +7 |

TABLE XVII-continued
EVALUATION OF TEST COMPOUND FOR INCREASING THE TOTAL WEIGHT OF POTATOES AND THE NUMBER OF U.S. NO. 1 POTATOES PRODUCED PER PLANT WHEN THE TEST COMPOUND IS APPLIED THREE WEEKS POST PLANTING - TWO WEEKS PRE-EMERGENCE

| Compound | Rate kg/ha | Tuber Fresh Weight % (±) Untreated Controls | |
|---|---|---|---|
| | | U.S. No. 1 | Total |
| | 0.125 | +1 | +3 |
| | 0.0625 | +9 | +11 |
| 1-Nitro-3-(α,α,α,4-tetrafluoro-m-tolyl)guanidine | 1.0 | +13 | +14 |
| | 0.5 | +5 | +4 |
| Untreated controls average yield: | 0.25 | +1 | +1 |
| 382 cwt/A U.S. No. 1, 412 cwt/A total | 0.125 | +2 | +4 |
| | 0.0625 | +5 | +5 |
| 1-(m-Methoxybenzyl)-3-nitroguanidine | 1.0 | +10 | +11 |
| Untreated controls average yield: | 0.5 | +6 | +6 |
| 362 cwt/A U.S. No. 1, 394 cwt/A total | 0.25 | +4 | +5 |
| | 0.125 | +4 | +5 |
| | 0.0625 | +4 | +5 |
| 1-(3,5-Dichlorophenyl)-3-nitro-guanidine | 1.0 | +11 | +7 |
| | 0.5 | +19 | +18 |
| Untreated controls average yield: | 0.25 | +10 | +12 |
| 364 cwt/A U.S. No. 1, 394 cwt/A total | 0.125 | +12 | +10 |
| | 0.0625 | +19 | +18 |
| 1-Nitro-3-(α,α,α,4-tetrafluoro-m-tolyl)guanidine | 1.0 | +16 | +12 |
| | 0.5 | +17 | +17 |
| Untreated controls average yield: | 0.25 | +11 | +12 |
| 382 cwt/A U.S. No. 1, 412 cwt/A total | 0.125 | +4 | +4 |
| | 0.0625 | +14 | +13 |
| 1-(m-Methoxybenzyl)-3-nitro-guanidine | 1.0 | +5 | +3 |
| | 0.5 | +10 | +9 |
| Untreated controls average yield: | 0.25 | +8 | +8 |
| 331 cwt/A U.S. No. 1, 366 cwt/A total | 0.125 | +9 | +8 |
| | 0.0625 | +7 | +7 |

(±) = Increase or decrease over untreated controls.

EXAMPLE 21

Evaluation of test compounds formulated as emulsifiable concentrates or aqueous dispersions to determine their efficacy for increasing the number of U.S. No. 1 potatoes and the total weight of potatoes produced per plant In this evaluation, white potatoes, variety-Superior, are planted during mid-April. Three weeks after the plants have emerged; plots, comprising two 9.6 meter rows, spaced 0.9 meters apart, are sprayed with an aqueous dispersion of one of the following formulations:

| (1) Compound | Percent W/V |
|---|---|
| 1-(3,5-Dichlorophenyl)-3-nitroguanidine | 11.0 |
| N—Methylpyrrolidone | 38.0 |
| Tenneco 500/100 aromatic solvent | 35.0 |
| Anionic-nonionic surfactant T-Mulz 339 emulsifier | 6.0 |
| Multifilm X-77 spreader-activator | 10.0 |
| | 100.0 |

Tenneco 500/100 aromatic solvent is a product of Tenneco Oil Company, Houston, Tex.; having the following characteristics:

| Specific gravity 15.56/15.56° C. | 0.860–0.875 |
|---|---|
| Acidity | No free acid |
| Flash, TCC min. °F. | 100 |
| Kouri-Butanol value - min. | 92 |
| Aromatics, Vol. % - min. | 95 |
| Distillation range temp. | Not below 290° F. |

Multifilm X-77 is a product of Colloidal Products Corporation, Sausalito, Calif.; having the following characteristics:

| Specific gravity 20/20° C. | 0.98 |
|---|---|
| Density lb./gal. at 20° C. | 8.20 |
| Surface tension, Dynes/cm at 20° C. | 31 |

T-Mulz 339 is a product of the Thompson-Hayward Chemical Company, Kansas City, Kans., and is a blend of anionic-nonionic emulsifying agents.

| | Percent W/V |
|---|---|
| (2) Compound | |
| 1-Nitro-3-(α,α,α,4-tetrafluoro m-tolyl)guanidine | 11.0 |
| NaOH | 2.3 |
| H₂O | 86.7 |
| | 100.0 |
| (3) Compound | |
| 1-(m-Methoxybenzyl)-3-nitroguanidine | 11.0 |
| N—Methylpyrrolidone | 57.0 |
| C₈–C₁₀ alcohol | 24.0 |
| Emulphor EL 620 | 8.0 |
| | 100.0 |

Emulphor EL 620 is a polyoxyethylated vegetable oil marketed by GAF Corporation, New York, N.Y.

The treated plants are cared for in accordance with normal cultural practices utilized in the growing of potatoes until they reach maturity. When said plants reach maturity, about 20 weeks after planting, they are harvested. The total number of U.S. No. 1 potatoes per plot and total weight of all potatoes per plot are determined.

Data obtained are reported in Table XVIII below.

TABLE XVIII

EVALUATION OF FORMULATED TEST COMPOUNDS TO DETERMINE THEIR EFFECTIVENESS FOR INCREASING PRODUCTION OF U.S. NO. 1 POTATOES AND TOTAL WEIGHT OF POTATOES PRODUCED PER PLANT

| FORMULATION | POTATOES PER PLANT | PERCENT INCREASE OR DECREASE OVER UNTREATED CONTROLS RATE KG/HA | | | |
|---|---|---|---|---|---|
| | | 0.5 | 0.25 | 0.125 | 0.0625 |
| #1 | | | | | |
| 1-(3,5-Dichloro-phenyl)-3-nitroguanidine | U.S. No. 1 | +4 | +5 | +6 | +6 |
| | Total | +4 | +5 | +6 | +6 |
| #2 | | | | | |
| 1-Nitro-3-(α,α,α,4-tetra-fluoro-m-)tolyl)guanidine | U.S. No. 1 | +6 | +2 | 0 | +6 |
| | Total | +8 | +3 | 0 | +6 |
| #3 | | | | | |
| 1-(m-Methoxy-benzyl)-3-nitroguanidine | U.S. No. 1 | +11 | +16 | +8 | +9 |
| | Total | +11 | +17 | +7 | +10 |

Untreated controls - U.S. No. 1 = 360 cwt/A; Total = 390 cwt/A.

EXAMPLE 22

Evaluation of formulated test compounds for increasing the total weight of potatoes produced per plant (Variety-Russett-Burbank)

Following the procedure of Example 21, except that the evaluations are conducted in the north-western United States using white potatoes, Variety-Russett-Burbank, the formulations #2 and #3 described in Example 21 are evaluated. Data obtained are reported in Table XIX below.

TABLE XIX

EVALUATION OF FORMULATED TEST COMPOUNDS FOR INCREASING THE TOTAL WEIGHT OF POTATOES PER PLANT (VARIETY - RUSSETT-BURBANK)

| FORMULATION | WEEK OF POST APPLICATION | PERCENT INCREASE OR DECREASE OVER UNTREATED CONTROLS RATE KG/HA | | | |
|---|---|---|---|---|---|
| | | 0.5 | 0.25 | 0.125 | 0.0625 |
| #2 | | | | | |
| 1-Nitro-3-(α,α,α,4-tetra-fluoro-m-tolyl)guanidine | 1 | −3 | 0 | +14 | +6 |
| | 2 | +8 | +10 | +9 | +11 |
| #3 | | | | | |
| 1-(m-Methoxy-benzyl)-3-nitroguanidine | 1 | −1 | −2 | +2 | +11 |
| | 2 | +6 | +14 | +4 | +2 |

Untreated controls = U.S. No. 1 = 465 cwt/A, Total = 494 cwt/A.

EXAMPLE 23

Evaluation of test compounds for increasing total potato yield and increasing production of U.S. No. 1 potatoes The following evaluations are conducted to evaluate a variety of test compounds as plant growth regulants effective for increasing the total weight of potatoes produced by potato plants and also for increasing the production of U.S. No. 1 potatoes produced by said plants.

In these tests, potato plants, Superior variety, are grown in tubs in the greenhouse. The tubs, 2 ft.×1 ft.×1 ft., each contain two plants, and two tubs per treatment are used for evaluation. Two weeks post-emergence the plants are sprayed with an aqueous-acetone (50/50) mixture containing 0.25% of a nonionic wetting agent (nonylphenol containing 9 mols of ethylene oxide, oleic acid, and isopropanol) and sufficient test compound to provide 1 kg/ha of test compound. The plants are grown to maturity and harvested. Results obtained are reported in Table XX below.

TABLE XX

EVALUATION OF TEST COMPOUNDS FOR INCREASING TOTAL POTATO YIELD AND INCREASING PRODUCTION OF U.S. NO. 1 POTATOES

| Treatment | Total Tuber Fresh Weight Percent (±) Untreated Controls | Total U.S. No. 1 Tuber Fresh Weight Untreated Controls |
|---|---|---|
| 1-(m-Cyanophenyl)-3-nitroguanidine | +4 | — |
| Methyl m-(3-nitro-guanidine)benzoate | +5 | +14 |
| 1-(m-Ethoxyphenyl)-3-nitroguanidine | +1 | +8 |
| 1-(4-Fluoro-m-tolyl)-3-nitroguanidine | +3 | — |
| 1-[m-(Difluoromethoxy)-phenyl]-3-nitroguanidine | +31 | — |
| 1-Nitro-3-[m-(2,2,2-tri-fluoro-1,1-dihydroxyethyl)-phenyl]guanidine | +9 | — |
| 1-(2-Fluoro-5-methylbenzyl)-3-nitroguanidine | +17 | +30 |
| 1-(2-Fluoro-5-methoxy-benzyl)-3-nitroguanidine | +9 | +26 |
| 1-(2-Fluoro-3-methyl-benzyl)-3-nitroguanidine | +13 | +22 |
| 1-Nitro-3-[m-(trifluoro-methoxy)phenyl]guanidine | +7 | +13 |

Untreated control average total yield: 337 Cwt/A.

EXAMPLE 24

Evaluation of test compounds for increasing sugar yield from sugar beets

In the following tests, sugar beets (*Beta vulgaris,* L.) are planted during the third week of March in field plots. The plants are cared for in accordance with normal practices employed in the raising of sugar beet crops, except that evaluation plots are sprayed, either 120 days or 60 days prior to harvest, with aqueous dispersions of test compound formulated as emulsifiable concentrates. When the plants reach maturity, the beets are harvested, and the sugar yield and raw juice purity determined for all treatments.

The formulated compositions evaluated in these tests are as follows:

| Compound | Percent W/V |
|---|---|
| (1) | |
| 1-Nitro-3-(α,α,α,4-tetrafluoro-m-tolyl)guanidine | 11.0 |
| N—Methylpyrrolidine | 38.0 |
| Substituted benzenes (aromatic solvent) | 35.0 |
| Alkylarylpolyoxyethylene glycol, fatty acid and propanol | 10.0 |
| Octylphenoxy polyethoxy ethanol (nonionic-surfactant) | 6.0 |
| | 100.0 |
| (2) | |
| 1-(m-Methoxybenzyl)-3-nitro-guanidine | 11.0 |
| N—Methylpyrrolidone | 38.0 |
| Alkylarylpolyoxyethylene glycol fatty acid and propanol | 10.0 |
| Substituted benzenes (aromatic solvent) | 35.0 |

| Compound | Percent W/V |
|---|---|
| Octylphenoxy polyethoxy ethanol (nonionic-surfactant) | 6.0 |
| | 100.0 |

Data obtained are reported in Tables XXI and XXII below.

In these evaluations, test compounds were found to be effective on sugar beets for increasing recoverable sugar yields. For example, the compound 1-(m-methoxy-benzyl)-3-nitroguanidine applied at 1.0–0.25 lb/A 60 days before harvest gave 611 lbs/A more recoverable sugar than the untreated controls which yielded 6,130 lbs/A of sugar.

TABLE XXI
EVALUATION OF TEST COMPOUNDS APPLIED 120 DAYS BEFORE HARVEST FOR INCREASING SUGAR YIELD FROM SUGAR BEETS (BETA VULGARIS, L.)

| | | PERCENT INCREASE OVER UNTREATED CONTROLS | | |
|---|---|---|---|---|
| FORMULATION | RATE KG/HA | PERCENT SUGAR | RAW JUICE PERCENT PURITY | RECOVERABLE SUGAR |
| (1) | | | | |
| 1-Nitro-3-(α,α,α,4-tetrafluoro-m-tolyl)guanidine | 1.0 | +5 | 0 | +1 |
| | 0.25 | +4 | +1 | +6 |
| | 0.0625 | +5 | +1 | +4 |
| (2) | | | | |
| 1-(m-Methoxybenzyl)-3-nitroguanidine | 1.0 | +3 | 0 | +7 |
| | 0.25 | +3 | +1 | +4 |
| | 0.0625 | +4 | 0 | +5 |
| Untreated controls | — | 14.49 | 90.25 | 18.37 |
| | | | | (6,130 lbs/A) |

TABLE XXII
EVALUATION OF TEST COMPOUNDS APPLIED 60 DAYS BEFORE HARVEST FOR INCREASING SUGAR YIELD FROM SUGAR BEETS (BETA VULGARIS, L.)

| | | PERCENT INCREASE OVER UNTREATED CONTROLS | | |
|---|---|---|---|---|
| FORMULATION | RATE KG/HA | PERCENT SUGAR | RAW JUICE PERCENT PURITY | RECOVERABLE SUGAR |
| (1) | | | | |
| 1-Nitro-3-(α,α,α,4-tetrafluoro-m-tolyl)guanidine | 1.0 | +2 | +1 | +8 |
| | 0.25 | +2 | +1 | +2 |
| | 0.625 | +2 | +1 | +4 |
| (2) | | | | |
| 1-(m-Methoxybenzyl)-3-nitroguanidine | 1.0 | +3 | +1 | +10 |
| | 0.25 | +1 | 0 | +10 |
| | 0.625 | +1 | 0 | +3 |
| Untreated controls | — | 14.62 | 90.17 | 18.22 |
| | | | | (6,183 lbs/A) |

EXAMPLE 25
Evaluation of test compounds as yield-enhancing agents for garlic (*Allium sativum* cv Balady)

In this evaluation, garlic bulbs are planted in the field at a seeding rate of 475 kg/ha. Test plots include two ridges, 0.6 meters wide and 10 meters in length. Thirty-one days after planting, the seedling plants are sprayed with an aqueous suspension of test compound which provides from 0.063 to 0.5 kg/ha of compound being evaluated. The aqueous suspension is prepared by dispersing an emulsifiable concentrate containing the test compound in water. The emulsifiable concentrate has the following composition:

| Compound | Percent W/W |
|---|---|
| Nitroguanidine test compound | 11.0 |
| N—Methylpyrrolidone | 38.0 |
| Tenneco 500/100 aromatic solvent | 35.0 |
| Anionic-nonionic surfactant T-Mulz 339 emulsifier | 6.0 |
| Multifilm X-77 spreader-activator | 10.0 |
| | 100.0 |

Six months after planting, the garlic is harvested, and the results obtained are reported in Table XXIII below.

TABLE XXIII
EVALUATION OF TEST COMPOUNDS AS YIELD-ENHANCING AGENTS FOR GARLIC

Fresh Weight of Bulbs

| Compound | kg/ha | % (±) Untreated Control |
|---|---|---|
| 1-(3,5-Dichlorophenyl)-3-nitroguanidine | 0.5 | +8 |
| | 0.125 | +5 |
| 1-Nitro-3-(α,α,α,4-tetrafluoro-m-tolyl)-guanidine | 0.125 | +13 |
| | 0.063 | +4 |
| 1-(m-Methoxybenzyl)-3-nitroguanidine | 0.5 | +9 |
| | 0.125 | +8 |

Untreated control average yield: 17.3 m Ton/ha

EXAMPLE 26
Evaluation of test compounds as yield-enhancing agents for carrots (*Daucus carota* cv chantenay)

In this evaluation, carrots are planted in fields at a seeding rate of 9 kg/hectare. Forty-six days after planting, the seedling plants are sprayed with aqueous-acetone (50/50) dispersion containing test compound and 0.25% of Multifilm X-77 spreader-activator. Plots used for evaluation include two ridges 0.6 meters wide and 10 meters in length. About four months after planting, the carrots are harvested, and the results obtained reported in Table XXIV below.

TABLE XXIV
EVALUATION OF NITROGUANIDINE TEST COMPOUNDS AS YIELD-ENHANCING AGENTS FOR CARROTS

| Compound | Rate kg/ha | Fresh Weight of Roots % (±) Untreated Control |
|---|---|---|
| 1-(3,5-Dichlorophenyl)-3-nitroguanidine | 0.5 | +1 |
|  | 0.125 | +6 |
| 1-Nitro-3-(α,α,α,4-tetrafluoro-m-tolyl)-guanidine | 0.125 | +17 |
|  | 0.063 | +26 |
| 1-(m-Methoxybenzyl)-3-nitroguanidine | 0.5 | +20 |
|  | 0.125 | +19 |

Untreated control average yield 26.0 m ton/ha

EXAMPLE 27

Evaluation of test compounds as yield-enhancing agents for turnips (*Brassica rapa* cv white purple top globe)

In this evaluation, test compound is dissolved in an acetone/water (50/50) mixture containing test compound and 0.25% of Multifilm X-77 spreader-activator. The test composition is applied post-emergently to the foliage of turnips eight or twelve weeks after planting. Plots used for evaluation are single rows, 10 feet long, arranged on 100 centimeter centers. Six replicates per treatment are used, and the turnips are harvested about four months after planting. Data obtained are reported in Table XXV below.

TABLE XXV
EVALUATION OF TEST COMPOUNDS AS YIELD-ENHANCING AGENTS FOR TURNIPS

| Treatment | Rate kg/ha | Fresh Weight of Roots % (±) Untreated Controls |
|---|---|---|
| 1-(m-Methoxybenzyl)-3-nitroguanidine Applied eight weeks post planting (Root thickness 1.25-2.5 cm) | 2.0 | +5 |
|  | 0.5 | +3 |
| 1-(m-Methoxybenzyl)-3-nitroguanidine Applied twelve weeks post planting (Root thickness 3.8-7.5 cm) | 2.0 | +29 |
|  | 0.5 | +5 |

Untreated control average yield: 332 cwt/acre.

EXAMPLE 28

Evaluation of test compounds as yield-enhancing agents for red table beets (*Beta vulgaris* cv green top bunching)

Following the procedure of Example 27 above, but substituting red table beets for turnips, demonstrates the yield-enhancing effects of the compounds of the invention on red table beets. Data obtained are reported in Table XXVI below.

TABLE XXVI
EVALUATION OF TEST COMPOUNDS AS YIELD-ENHANCING AGENTS FOR RED TABLE BEETS

| Treatment | Rate kg/ha | Fresh Weight of Roots % (±) Untreated Controls |
|---|---|---|
| 1-(m-Methoxybenzyl)-3-nitroguanidine Applied eight weeks post planting (Plant height 7.5-15 cm) | 2.0 | +13 |
|  | 0.5 | +5 |

TABLE XXVI-continued
EVALUATION OF TEST COMPOUNDS AS YIELD-ENHANCING AGENTS FOR RED TABLE BEETS

| Treatment | Rate kg/ha | Fresh Weight of Roots % (±) Untreated Controls |
|---|---|---|
| 1-(m-Methoxybenzyl)-3-nitroguanidine Applied 12 weeks post planting (Plant height 20-40 cm) | 2.0 | +14 |
|  | 0.5 | −2 |

EXAMPLE 29

Evaluation of test compounds as yield-enhancing agents for tulips [(*Tulipa sylvestris* cv Iverson (albino)]

In this evaluation, field-grown tulips are treated when about 100% of the tulips are in bud or when all are in late bloom. The plants are sprayed with an aqueous-/acetone mixture (20/80) containing test compound and 0.25% Multifilm X-77 spreader-activator. Plot sizes utilized in this evaluation are 1 row×5 ft. long with each treatment replicated six times. Bulbs are harvested six weeks after the late bloom treatment. Data obtained are reported in Table XXVII below.

TABLE XXVII
EVALUATION OF TEST COMPOUNDS AS YIELD-ENHANCING AGENTS FOR TULIPS

| Treatment | Rate kg/ha | Large Bulbs Fresh Weight % (±) Untreated Controls | Percent of Large Bulbs |
|---|---|---|---|
| 1-(m-Methoxybenzyl)-3-nitroguanidine (100% in bud) | 2.0 | +26 | +35 |
|  | 0.5 | +80 | +81 |
| 1-(m-Methoxybenzyl)-3-nitroguanidine (Full bloom) | 2.0 | 0 | +5 |
|  | 0.5 | +53 | +49 |

EXAMPLE 30

Evaluation of test compounds as yield-enhancing agents for sunflowers (*Helianthus annus* cv Dohlgren D0164)

In this evaluation, sunflowers growing in 18 cm pots, spaced in rows 75 cm apart, are treated at the V8, V11-12, V16, V20 (R1) or V22 (R2-5) stage of growth with aqueous dispersion of test compound. Test compounds are dispersed in acetone/water mixtures (2:1 ratio) containing 0.25% of a nonionic wetting agent (i.e., nonylphenol containing 9 moles of ethylene oxide, oleic acid, and isopropanol). The dispersions are applied as aqueous sprays in sufficient amounts to provide 0.31 kg/ha thereof to the test pots. Five months after planting, the seed heads are harvested, and the weight of seeds from each plant is determined. Data obtained are reported in Table XXVIII below.

TABLE XXVIII
EVALUATION OF TEST COMPOUNDS AS YIELD-ENHANCING AGENTS FOR SUNFLOWERS

| Treatment | Rate kg/ha | Fresh Weight of Seeds % (±) Untreated Controls |
|---|---|---|
| 1-(3,5-Dichlorophenyl)-3-nitroguanidine Applied at the following vegetative stages: |  |  |
| V8 | 0.31 | +17 |
| V11-12 | 0.31 | +37 |
| V16 | 0.31 | +26 |
| V20 (R1) | 0.31 | +29 |

TABLE XXVIII-continued
EVALUATION OF TEST COMPOUNDS AS YIELD-ENHANCING AGENTS FOR SUNFLOWERS

| Treatment | Rate kg/ha | Fresh Weight of Seeds % (±) Untreated Controls |
|---|---|---|
| V22 (R2-5) | 0.31 | +5 |

EXAMPLE 31

Evaluation of test compounds as yield-enhancing agents for tobacco (*Nicotiana tabacum* cv Coker 319)

In this evaluation, Coker 319 variety tobacco plants are grown in 22.5 cm plastic pots, one plant per pot. The pots are placed in rows 50 cm apart, and four to six replicates per treatment are used for evaluation.

When the plants are 5, 45 or 115 centimeters in height, they are sprayed with an aqueous dispersion of test compound previously formulated as a liquid flowable formulation. The liquid flowable formulation contains, on a percent w/w basis, 30% 1-(3,5-dichlorophenyl)-3-nitroguanidine, 0.4% colloidal magnesium aluminum silicate, 1.5% naphthalene formaldehyde condensate, 8% polyethylene glycol, 0.1% nonylphenol ethylene oxide condensate (9–11 moles ethylene oxide), 0.1% sodium lignosulfonate, 0.07% citric acid, 0.06% xanthan gum, 59.67% water and 0.10% paraformaldehyde. The liquid flowable formulation is diluted with water and 0.25% of the Multifilm X-77 spreader-activator (alkylarylpolyoxyethylene glycols, free fatty acids and isopropanol) in the spray tank. The dispersion is sprayed on the plants in sufficient amounts to provide 0.25 kg/ha of test compound. The plants are grown to maturity and then harvested. Data obtained are reported in Table XXIX below. It is also noted that treatment of the tobacco plants retards senescence of the lower tobacco leaves and permits harvesting of all leaves in a single cutting.

TABLE XXIX
EVALUATION OF TEST COMPOUNDS AS YIELD-ENHANCING AGENTS FOR TOBACCO

| Treatment | Rate kg/ha | Dry Weight of Leaves % (±) Untreated Controls |
|---|---|---|
| 1-(3,5-Dichlorophenyl)-3-nitroguanidine Applied at the following plant heights: | | |
| 5 cm | 0.25 | +38 |
| 45 cm | 0.25 | +64 |
| 115 cm | 0.25 | +112 |

EXAMPLE 32

Evaluation of test compounds as yield-enhancing agents for onion (*Allium cepa* cv Italian Red)

In this evaluation, onions (Italian Red variety) are field planted, one plant per 10 centimeters. Treatment plots used for evaluation include two ridges 0.6 meters wide and 10 meters in length. Thirty-seven days after planting, test plots are sprayed with an aqueous dispersion of one of the following formulations:

| | Percent W/W |
|---|---|
| (1) | |
| 1-(3,5-Dichlorophenyl)-3-nitroguanidine | 11 |
| Tenneco 500/100 aromatic solvent | 35 |
| Anionic-nonionic surfactant | 6 |
| T-Mulz 339 emulsifier | |
| Multifilm X-77 spreader-activator | 10 |
| N—Methylpyrrolidone | 38 |
| | 100 |
| (2) | |
| 1-(m-Methoxybenzyl)-3-nitroguanidine | 11 |
| Tenneco 500/100 aromatic solvent | 35 |
| Anionic-nonionic surfactant | 6 |
| T-Mulz 339 emulsifier | |
| Multifilm X-77 spreader-activator | 10 |
| N—Methylpyrrolidone | 38 |
| | 100 |
| (3) | |
| 1-Nitro-3-(α,α,α,4-tetrafluoro-m-tolyl)guanidine | 11 |
| Tenneco 500/100 aromatic solvent | 35 |
| Anionic-nonionic surfactant | 6 |
| T-Mulz 339 emulsifier | |
| Multifilm X-77 spreader-activator | 10 |
| Tetrahydrofuran | 38 |
| | 100 |

Four months after treatment, the onions are harvested and the results obtained are reported in Table XXX below.

TABLE XXX
EVALUATION OF TEST COMPOUNDS AS YIELD-ENHANCING AGENTS FOR ONIONS

| Compound | Rate kg/ha | Fresh Weight Per Bulb % (±) Untreated Controls |
|---|---|---|
| 1-(3,5-Dichloro-phenyl)-3-nitro-guanidine | 0.5 | +32 |
|  | 0.125 | +22 |
| 1-Nitro-3-(α,α,α,4-tetrafluoro-m-tolyl)-guanidine | 0.125 | +25 |
|  | 0.063 | +32 |
| 1-(m-Methoxybenzyl)-3-nitroguanidine | 0.5 | +21 |
|  | 0.125 | +23 |

Untreated control average yield: 177 grams/bulb.

EXAMPLE 33

Evaluation of test compounds as yield-enhancing agents for rutabaga (*Brassica napus*, variety napobrassica)

The test procedure employed for evaluation of test compounds as yield-enhancing agents for rutabagas is as follows: The rutabagas are planted in early May; two months thereafter they are sprayed with an aqueous suspension of test compounds formulated as liquid flowable formulations described in Example 31. The rutabagas are harvested about four months after planting, and the data are reported in Table XXXI below.

TABLE XXXI
EVALUATION OF TEST COMPOUNDS AS YIELD-ENHANCING AGENTS FOR RUTABAGAS

| Compound | Rate kg/ha | Fresh Weight Per Tuber % (±) Untreated Controls |
|---|---|---|
| 1-Nitro-3-(α,α,α-trifluoro-m-tolyl)-guanidine | 0.125 | +54 |
|  | 0.5 | +3 |
| 1-(3,5-Dichloro-phenyl)-3-nitro-guanidine | 0.125 | +39 |
|  | 0.5 | +3 |
| 1-(m-Methoxybenzyl)-3-nitroguanidine | 0.125 | +19 |
|  | 0.5 | +8 |

Untreated control average yield: 510 g/tuber

EXAMPLE 34

Evaluation of test compounds as yield-enhancing agents for alfalfa (*Medicago sativa*, cv Saranoc)

In this evaluation, aqueous dispersions of test compounds are sprayed pre-emergently on 12.5 × 12.5 cm fiber pots planted with alfalfa seeds. Each pot contains four plants, and each treatment is replicated five times. The evaluation test compounds are dispersed in acetone/water (50/50) mixtures with 0.25% w/w of a nonionic wetting agent (nonylphenol containing 9 mols of ethylene oxide, oleic acid, and isopropanol) added. Six weeks after spraying at the first bloom stage of growth, the alfalfa is clipped, and the number of alfalfa stems per pot is determined. Data obtained are reported in Table XXXII below.

TABLE XXXII
EVALUATION OF TEST COMPOUNDS AS YIELD-ENHANCING AGENTS FOR ALFALFA

| Compound | Rate kg/ha | Number of Stems Per Pot |
|---|---|---|
| 1-(3,5-Dichloro-phenyl)-3-nitro-guanidine | 0.06 | 11.8 |
|  | 0.03 | 12.4 |
|  | 0.015 | 14.4 |
|  | 0.0075 | 14.8 |
| Untreated control | — | 11.2 |

EXAMPLE 35

Evaluation of test compounds as yield-enhancing agents for tomatoes (*Lycopersicon esculentum*)

To evaluate test compounds as yield-enhancing agents for tomatoes, process tomatoes are planted in two-row beds with 45 centimeters between rows. Each plot consists of two rows, six meters in length, and plots are sprayed with aqueous dispersions of test compound when the plants reach first bloom. Compounds being evaluated are formulated as described in Example 32. Aqueous dispersions are applied in sufficient amount to provide about 1.0 kg/ha of test compound to the treated plots, and data are taken when the tomatoes begin to ripen. Data obtained are reported in Table XXXIII below.

TABLE XXXIII
EVALUATION OF TEST COMPOUNDS AS YIELD-ENHANCING AGENTS FOR TOMATOES

| Compound | Rate kg/ha | Kg. Tomatoes/Six Meter Row for Two-Row Beds |
|---|---|---|
| Untreated control | — | 106.8 |
| 1-(m-Methoxybenzyl)-3-nitroguanidine | 1.0 | 113.8 |

EXAMPLE 36

Evaluation of test compounds for extending the shelf life of cut flowers, i.e., daffodils (*Narcissus pseudonarcissus*)

Daffodils are picked with fully-opened flower buds on the morning of the experiment. Stems are re-cut to 30 cm lengths and, within one-half hour of harvest, flower stems are immersed to a depth of 10 cm in 2,000 ml of the treating solution. The treating solution contains the test compound at 100 ppm. It is prepared by dissolving 100 mg of 1-nitro-3-($\alpha,\alpha,\alpha$,4-tetrafluoro-m-tolyl)guanidine in 100 ml acetone and bringing the volume to 2,000 ml with deionized water. Control solutions consist of 5% acetone in water and water alone.

After immersion in the test solution for three minutes, 30 minutes, 90 minutes, 270 minutes, or 24 hours, three specimens, selected at random, are transferred to 450 ml deionized water in 0.5-liter, wide-mouth amber jars and held there until the experiment is terminated; three specimens remain in the treating solution for the duration of the test. Stems of control flowers are held in 5% acetone for 30 minutes and 24 hours (three specimens for each immersion time) before transferring to deionized water while three specimens remain in water for the duration of the experiment. Treatments are distributed randomly in the laboratory maintained at about 21° C.-25° C. Normal daylight is supplemented with fluorescent lighting to provide 12-hour periods of light and dark.

Flowers are rated for decorative value two days and four days post-treatment. Each specimen is separately rated for appearance of perianth and corona according to the scale shown below wherein increasing numerical value indicates increasing senescence. An unweighted mean value representing the overall appearance of the flower is then assigned to the treatment.

| Decorative Acceptability | Numerical Rating | Description |
|---|---|---|
| A. Perianth | | |
| Acceptable | 1 | Fresh appearance, perianth smooth and flat, no visual evidence of senescence |
| Acceptable | 2 | Slight curling at margin |
| Acceptable | 3 | Slight wilting |
| Acceptable | 4 | Marginal discoloration (browning) and increased wilt |
| Unacceptable | 5 | Pigment loss (translucence) in less than half perianth |
| Unacceptable | 6 | Pigment loss (translucence) in more than half perianth |
| Unacceptable | 7 | Completely desiccated and/or brown. |
| B. Corona | | |
| Acceptable | 1 | Erect and firm |
| Acceptable | 2 | Expanding and flattening |
| Acceptable | 3 | Slight wilt, margin discolored (brown) |
| Unacceptable | 4 | Less than half wilted and/or brown, desiccated |
| Unacceptable | 5 | More than half wilted and/or brown, desiccated. |

TABLE XXXIV
EXTENDED VASE LIFE OF DAFFODILS TREATED FOR VARIOUS LENGTHS OF TIME IN 100 PPM of 1-NITRO-3-($\alpha,\alpha,\alpha$,4-TETRAFLUORO-m-TOLYL)GUANIDINE

| Treatment | Immersion Time | Flower Freshness At Indicated Time Post Treatment | |
|---|---|---|---|
| | | Two Days | Four Days |
| 1-Nitro-3-($\alpha,\alpha,\alpha$,4-tetrafluoro-m-tolyl)-guanidine | 3 minutes | 1.8 | 2.5 |
| | 30 minutes | 1.7 | 2.5 |
| | 90 minutes | 1.7 | 2.7 |
| | 270 minutes | 1.3 | 2.2 |
| 1-Nitro-3-($\alpha,\alpha,\alpha$,4-tetrafluoro-m-tolyl)-guanidine | 24 hours | 1.3 | 2.2 |
| 1-Nitro-3-($\alpha,\alpha,\alpha$,4-tetrafluoro-m-tolyl)-guanidine | Duration | 1.5 | 2.7 |
| Acetone Control | 30 minutes | 2.2 | 3.5 |

TABLE XXXIV-continued
EXTENDED VASE LIFE OF DAFFODILS TREATED
FOR VARIOUS LENGTHS OF TIME IN 100 PPM of
1-NITRO-3-(α,α,α,4-
TETRAFLUORO-m-TOLYL)GUANIDINE

| Treatment | Immersion Time | Flower Freshness At Indicated Time Post Treatment | |
|---|---|---|---|
| | | Two Days | Four Days |
| Acetone Control | 24 hours | 2.3 | 3.8 |
| Water Control | Duration | 2.2 | 3.3 |

The test is continued after the flowers have lost fresh-flower decorative value in order to continue observations on the stems. (J. L. Stoddart in *British Plant Growth Regulator Group*, Monograph No. 8, page 1, in part defines senescence in plants as follows: "More precisely, in leaves, it relates to the loss of structural integrity and photosynthetic competence in the chloroplast.") Retention of chlorophyll in daffodil flower stem (or scape) treated with the subject compound after untreated stems are depleted of chlorophyll, i.e., have turned yellow or brown, is indicative of delayed senescence.

In this test, the flower stem is rated for color and general appearance at 17 days and 25 days post treatment. Flower stems (scapes) are rated individually for color and turgidity and assigned numerical ratings as shown in the following Table XXXV. Increasing numerical value denotes progressive loss of photosynthetic competence, depletion of chlorophyll, and loss of structural integrity; in sum, increasing senescence terminating in death.

RATING SYSTEM
SENESCENCE RATING OF DAFFODIL
CUT FLOWER STEMS (SCAPES)

| Numerical Rating | Predominant Color and Appearance |
|---|---|
| 1 | Green, turgid, i.e., little or no visual evidence of senescence |
| 2 | Gray-green, turgid, i.e., slight senescence |
| 3 | Yellow-green, turgid |
| 4 | Yellow, turgid |
| 5 | Yellow-brown, turgid, i.e., advanced senescence |
| 6 | Brown, erect, i.e., complete senescence |
| 7 | Brown, collapsed, death |

TABLE XXXV
DELAYED SENESCENCE OF DAFFODIL CUT FLOWER
STEMS (SCAPES) TREATED WITH 100 PPM of 1-NITRO-
3-(α,α,α,4-TETRAFLUORO-m-TOLYL)GUANIDINE

| Treatment | Immersion Time | Stem Color and Appearance At Indicated Time Post Treatment | |
|---|---|---|---|
| | | 17 Days | 25 Days |
| 1-Nitro-3-(α,α,α,4-tetra-fluoro-m-tolyl)-guanidine | 3 minutes | 1.3 | 1.3 |
| | 30 minutes | 1.0 | 2.0 |
| | 90 minutes | 1.3 | 4.0 |
| | 270 minutes | Not Rated | 1.0 |
| 1-Nitro-3-(α,α,α,4-tetra-fluoro-m-tolyl)-guanidine | 24 hours | 1.3 | 5.3 |
| 1-Nitro-3-(α,α,α,4-tetra-fluoro-m-tolyl)-guanidine | Duration | 4.0 | 7.0 |
| 5% Acetone Control | 30 minutes | 4.7 | 7.0 |
| 5% Acetone Control | 24 hours | 5.7 | 7.0 |
| Water Control | Duration | 5.3 | 7.0 |

EXAMPLE 37
Evaluation of test compounds as yield-enhancing agents for alfalfa The procedure of Example 34 is repeated except that 1-(3,5-dichlorophenyl)-3-nitroguanidine is applied at rates of from 3.5 g/ha to 20 g/ha with the results of the tests reported as alfalfa dry weight (±) percent of control. Data are reported in Table XXXVI below.

TABLE XXXVI
EVALUATION OF TEST COMPOUNDS AS YIELD
ENHANCING AGENTS FOR ALFALFA

| Compound | Alfalfa dry weight (±) % of control |
|---|---|
| Untreated control | — |
| 1-(3,5-Dichlorophenyl)-3-nitroguanidine | |
| 20 g/ha | +8.0 |
| 15 g/ha | +20.0 |
| 7.5 g/ha | +39.0 |
| 3.5 g/ha | +25.0 |

EXAMPLE 38
Evaluation of test compounds as yield enhancing agents for apples In this evaluation test compounds are dispersed in 50/50 acetone/water mixtures in sufficient quantity to provide dispersions or solutions containing 0, 10, 100 or 1000 ppm of active ingredient and about 0.25% by volume of a nonionic wetting agent (nonylphenol) containing 9 mols of ethylene oxide, oleic acid and isopropanol). Test dispersions are applied to apple (*Malus sylvestris* Mill. cv. Oregon Spur Delicious) trees in the spring at the time of peak bloom. All test solutions are sprayed to run off. Each treatment utilizes two trees selected at random from a block of uniformly blossoming individuals. During the growing season, the orchard in which the experiment is conducted is sprayed with normal fungicides and insecticides. Treatments are consistent with recommended cultural practices. At the end of the season, fruit from each tree is harvested, weighed and the average weight of fruit per tree determined. The results are reported in Table XXXVII below.

TABLE XXXVII
EVALUATION OF TEST COMPOUNDS AS
YIELD ENHANCING AGENTS FOR APPLES

| Compound | Rate (ppm) | Average yield tree (lb. of fruit) |
|---|---|---|
| 1-(3,5-Dichloro-phenyl)-3-nitro-guanidine | 1000 | 57.5 |
| | 100 | 61.5 |
| | 10 | 62.3 |
| Control | 0 | 39.3 |
| 1(m-Methoxybenzyl)-3-nitroguanidine | 1000 | 36.3 |
| | 100 | 62.8 |
| | 10 | 58.5 |

TABLE XXXVII-continued

EVALUATION OF TEST COMPOUNDS AS
YIELD ENHANCING AGENTS FOR APPLES

| Compound | Rate (ppm) | Average yield tree (lb. of fruit) |
|---|---|---|
| Control | 0 | 47.5 |

EXAMPLE 39

Extended shelf life of swiss chard

The deterioration of cut leaves of swiss chard is slowed following a brief dip of the leaves in a solution containing 1-(m-methoxybenzyl)-3-nitroguanidine in acetone to produce concentrations of test compound in the range of 8 to 512 ppm. Leaves are cut from field-grown swiss chard plants and each leaf is cut in half lengthwise, with one piece being dipped for 60 seconds in test solution and the second for 60 seconds in a solution of $H_2O$ and the appropriate control level of acetone (no separate acetone effect is observed). The leaf pieces are drained and then laid in trays with moist toweling. After four days at 20° C., the trays are exposed to 30° C. for another four days. Senescence is monitored by visual observation of the loss of chlorophyll and/or progression of necrosis of the leaves. The effective concentration range is above 8 or 64 ppm.

| Treatment (ppm) 1-(m-methoxybenzyl-3-nitroguanidine | Retardation of Senescence, % of control |
|---|---|
| 1 | 0 |
| 8 | 25 |
| 64 | 70 |
| 512 | 75 |

EXAMPLE 40

Extending vase life of cut gladiolus flowers by treating with substituted nitroguanidines The vase life of cut flowers is the length of time that the flower retains its decorative value. Vase life is, in part, determined by the cut stem's ability to continue to conduct nutrients and water to, and provide support for the flower. The ability is especially important for flowers whose stems bear many florets, such as, for example, the gladiolus. When such flowers are cut with closed buds which eventually open while in the vase and when bud-opening is acropretally with time, maximum vase life is especially dependent upon a functioning stem.

Gladiolus flowers are obtained from a local nursery distributor and transported to the laboratory wrapped and boxed as customary in the trade. Stems are recut to 30 cm lengths in a cold-room maintained at 4° C. and 60% rh and immersed in a solution, hereafter referred to as the treating solution of the following composition:

| Component | g/l |
|---|---|
| Sucrose | 20.00 |
| Citric acid, monohydrate | 4.20 |
| 8-Hydroxyquinoline citrate | 0.20 |
| Deionized water | ca.900 ml |
| Reaction adjusted to pH 4.6 with 10 molar solution of potassium hydroxide (about 3.9 mL/l of medium). | |
| Deionized water | qs 1000 ml |

Jars are distributed at random around the laboratory which is maintained at 21° C. to 25° C. Normal daylight is supplemented with fluorescent lighting to provide 12 hour periods of light. Appropriate holding solution is replenished as needed.

Flowers are rated for decorative value five days post-treatment. The overall appearance of all open florets on each of the five stems per replicate (two replicates per treatment) is assigned a single rating based on the scale shown below in which increasing numerical value indicates increasing senescence. The rating provides a single value which reflects the range of the severity of wilting or senescence shown by the individual florets on each stem.

| Freshness rating of cut gladiolus Flower: Severity of floret wilt and browning | | |
|---|---|---|
| Decorative Acceptability | Numerical Score | Description |
| Acceptable | 1 | Fresh, no wilt |
| | 1.5 | Trace wilt (curl) @ margin |
| | 2 | Slight wilt extending beyond margin |
| | 2.5 | Moderate wilt with slight marginal browning |
| Unacceptable | 3 | Pronounced wilt and browning |
| | 3.5 | Severe wilt, browning with areas of desiccation |
| | 4 | Complete wilt and desiccation |

An additional rating, based on the scale shown below, is assigned to reflect the extent of the wilting, i.e., the proportion of wilted florets.

| Freshness rating of cut gladiolus Flowers: Extent of wilting | |
|---|---|
| Decorative Acceptability | Proportion of wilted florets % |
| Acceptable | 0 |
| | 0–10 |
| | 10–25 |
| | 25–50 |
| Unacceptable | 50–75 |
| | 75–100 |
| | 100 |

The numbers of open florets and healthy opening buds, i.e., buds exposing at least 1 cm length of petal with no visible discoloration, step color and turgor, and bud color, are also recorded. Color changes accompanying senescence are shown in the rating system below.

| Freshness rating of cut gladiolus stem by color | | |
|---|---|---|
| Rating | Color | Increasing Senescence |
| Dk gn | Dark green | ↓ |
| Gn | Green | ↓ |
| YG | Yellow-green | ↓ |
| Y | Yellow | ↓ |
| Br | Brown | ↓ |

The results of this experiment are shown below in Table XXXVIII.

TABLE XXXVIII

Extended vase life of cut gladiolus flowers treated with 100 ppm solutions of several substitution nitroquanidines

| Treatment | Number of Open Florets | Number of Opening Buds | Floret wilt Extent % | Floret wilt Severity | Stem wilt | Color of Stem | Color of Bud |
|---|---|---|---|---|---|---|---|
| Untreated (DIW) | 19 | 5 | 50–75 | 3.0 | sh/med | Y6 | Y6/Br |
| Control (DIW) | 25 | 9 | 10–25 | 2.5 | slt | YG/Gn | YG/Gn |
| Control (Ac) | 21 | 11 | 10–25 | 2.5 | slt | YG/Gn | Y6 |
| 1-Nitro-3-(α,α,α-trifluoro-m-tolyl)guanidine | 23 | 42 | 0 | 1.0 | nil | Dk Gn | Gn |
| 1-((3,5-dichlorophenyl)-3-nitroguanidine | 49 | 15 | 0 | 1.0 | nil | Dk Gn | Gn |
| 1-Nitro-3-(α,α,α,4-tetrafluoro-m-tolyl)-guanidine | 17 | 37 | 0 | 1.0 | nil | Dk Gn | Gn |
| 1-(m-methoxybenzyl)-3-nitroguanidine | 42 | 21 | 0 | 1.0 | mL | Dk Gn | Gn |
| AOAA | 18 | 35 | 0–10 | 1.5 | nil | Dk Gn | Gn |

It is seen that treating cut gladiolus flowers by immersing stems for 30 minutes in solutions of substituted nitroguanidines substantially extends the vase life of such flowers as compared to the vase life of flowers not so treated. The extension so obtained is based on several criteria including, increased number of acceptable open florets, increased number of healthy opening buds, reduction in both severity and extent of floret wilt, superior retention of green color in stems and buds, and superior retention of stem turgor.

EXAMPLE 41

Delayed senescence in leafy green vegetables

Kale and collard greens are bought at local farmers market and refrigerated in plastic bags until needed. The outermost leaves are discarded, and young, healthy, undamaged leaves are used for the experiment. Leaves are removed from the stalk by cutting with a sharp scalpel at the point of attachment. Immediately after removal, the petiole is inserted into the treating solutions contained in 4 ounce wide-mouth amber jars. In order to provide support for the leaf and to minimize loss of solution by evaporation, the jars are stoppered with plastic foam plugs which previously had a radial cut made with a scalpel to accommodate the leaf petiole.

A treating solution with the experimental compound at 100 ppm is prepared by dissolving 200 mg of 1-nitro-3-(α,α,α,4-tetrafluoro-m-tolyl)guanidine in 100 ml acetone and bringing to a final volume of 2000 ml with deionized water. Treating solutions with the experimental compound at 10 ppm and 1 ppm are made by 10 fold serial dilution using 5% aqueous acetone as the diluent. Control solutions consisting of 5% aqueous acetone and water alone are included in the experiment.

All treatments, with both kale and collard greens, are replicated four times, each replicate leaf deriving from a different plant. The jars are randomly distributed throughout the laboratory maintained at 21° C. to 25° C. Normal daylight is supplemented by fluorescent lighting to provide 12 hour periods of light and dark. The treating solutions are replenished as needed using a funnel with its stem inserted through the radial cut of the foam stopper. Leaves are rated for retention of green color at one, three and seven days after initiation of treatment. Color changes accompanying advancing senescence are shown in the rating system below.

| Color Code | Color | Increasing Senescence |
|---|---|---|
| 1 | Dark Green | ↓ |
| 2 | Green | ↓ |
| 3 | Light Green | ↓ |
| 4 | Yellow Green | ↓ |
| 5 | Yellow | ↓ |
| 6 | Brown | ↓ |

The average ratings for the treatments on each of the observation days are shown in Table XL.

TABLE XL

RETENTION OF CHLOROPHYL AND DELAY OF SENESCENCE IN ISOLATED KALE AND COLLARD LEAVES TREATED WITH SOLUTIONS 1-NITRO-3-(α,α,α,4-TETRAFLUORO-M—TOLYL)GUANIDINE

| Concentration of 1-nitro-3-(α,α,α,-4-tetrafluoro-m-tolyl)guanidine PPM | Leaf color after 1,3 and 7 days after treatment Kale | | | Collard | | |
|---|---|---|---|---|---|---|
| | 1 | 3 | 7 | 1 | 3 | 7 |
| 100 | 1.0 | 1.0 | 1.8 | 1.0 | 1.1 | 2.8 |
| 10 | 1.0 | 1.0 | 1.0 | 1.0 | 1.0 | 3.5 |
| 1 | 1.0 | 1.0 | 2.0 | 1.0 | 1.3 | 3.7 |
| 0 (5% acetone) | 1.0 | 1.0 | 5.3 | 1.0 | 2.3 | 4.5 |
| 0 (DIW) | 1.0 | 2.0 | 5.3 | 1.0 | 3.3 | 3.8 |

These results demonstrate the delay of onset and progress of senescence in treated leaves.

What is claimed is:

1. Guanidine compounds represented by the following formulae:

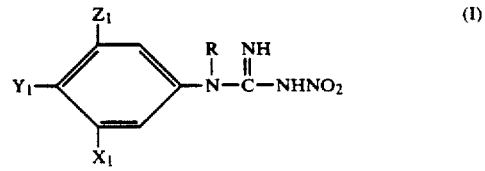

(I)

wherein $X_1$ is $COCH_3$, halogen, CN, $CH_2CN$, $C(OH)_2CF_3$, $OCHF_2$, $OCF_3$, $CH_3$, $CF_3$, $NO_2$, $OCF_2CHF_2$, $OCH_3$, $N(CH_3)_2$, or $CH_2OR_3$ where $R_3$ is H or $CH_3$;

$Y_1$ is H, halogen, $CH_3$;

$Z_1$ is H, $CH_3$, halogen, $OCH_3$ or $CF_3$;

R is H or $CH_3$;

with the provisos that when $X_1$ is $CH_3$, $OCH_3$, F, Cl or Br and R is H, then $Y_1$ and $Z_1$ cannot both be hydrogen; and when $X_1$ is Cl and $Z_1$ and R are each hydrogen, then $Y_1$ cannot be methyl;

and the salts or tautomers thereof;

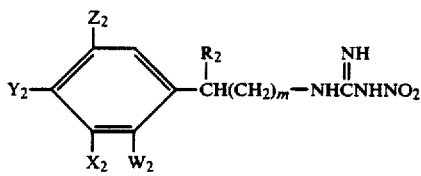
(II)

wherein $X_2$ is H, OH, straight or branched $C_1$-$C_4$ alkoxy, halogen, $OCF_3$, $CF_3$, straight or branched $C_1$-$C_4$ alkyl or $Y_2$ is H or F;

$Z_2$ is F, H, $CH_3$ or $OCH_3$;

$W_2$ is or F;

m is an integer of 0, 1, or 2;

$R_2$ is H, $CH_3$, $C_2H_5$ or $CF_3$;

with the provisos that when m is 0 and $R_2$ is or $CH_3$, then $W_2$, $X_2$, $Y_2$ and $Z_2$ cannot all be hydrogen;

and when m is 1, then $R_2$, $W_2$, $X_2$, $Y_2$ and $Z_2$ cannot all be hydrogen; and the salts or tautomers thereof;

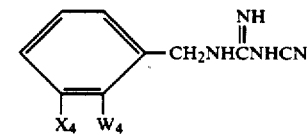
(IV)

wherein $W_4$ is H or F and $X_4$ is straight or branched $C_1$-$C_4$ alkoxy, straight or branched $C_1$-$C_4$ alkyl or F;

with the provisos that when $W_4$ is F, $X_4$ is H; and the salts or tautomers thereof.

2. Guanidine compounds according to claim 1, said compounds represented by structural formula,

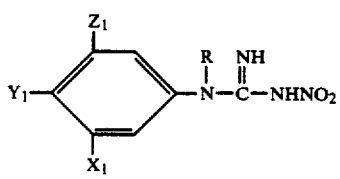

wherein $X_1$, $Y_1$, $Z_1$, and R are as described in claim 1; and the salts or tautomers thereof.

3. Guanidine compounds according to claim 1, said compounds represented by structural formula,

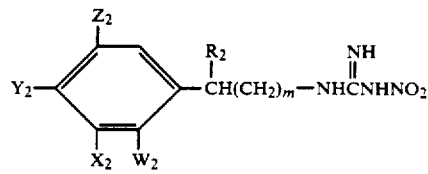

wherein $W_2$, $X_2$, $Y_2$, $Z_2$, $R_2$, and m are as described in claim 1; and the salts or tautomers thereof.

4. Guanidine compounds according to claim 1, said compounds represented by structural formula, wherein $W_4$ and $X_4$ are as described in claim 1, and the salts or tautomers thereof.

5. Guanidine compounds according to claim 2, wherein said compound is 1-nitro-3-($\alpha,\alpha,\alpha$,4-tetrafluoro-m-tolyl) guanidine.

6. Guanidine compounds according to claim 3, wherein said compound is 1-(m-methoxybenzyl)-3-nitroguanidine.

7. Guanidine compounds according to claim 2, wherein said compound is 1-(3,5-dichlorophenyl)-3-nitroguanidine.

8. Guanidine compounds according to claim 2, wherein said compound is 1-nitro-($\alpha,\alpha,\alpha$,-trifluoro-m-tolyl) guanidine.

9. Guanidine compounds according to claim 3, wherein said compound is 1-(o-fluorobenzyl)-3-nitroguanidine.

10. Guanidine compounds according to claim 3, wherein said compound is 1-(2-fluoro-5-methoxybenzyl)-3-nitroguanidine.

11. Guanidine compounds according to claim 2, wherein said compound is 1-(m-acetylphenyl)-3-nitroguanidine.

12. Guanidine compounds according to claim 3, wherein said compound is 1-(p-fluorobenzyl)-3-nitroguanidine.

13. Guanidine compounds according to claim 2, wherein said compound is 1-[m-(difluoromethoxy)-phenyl]-3-nitroguanidine.

14. Guanidine compounds according to claim 2, wherein said compound is 1-(4-chloro-alpha,alpha,alpha,-trifluoro-m-tolyl)-3-nitroguanidine, 1-nitro-3-[m-(2,2,2-trifluoro-1,1,-dihydroxyethyl)phenyl]guanidine, 1-(3,4-dichlorophenyl)-3-nitroguanidine, 1-(4-bromo-m-tolyl)-3-nitroguanidine, 1-(3-chloro-4-fluorophenyl)-3-nitroguanidine, 1-(4-chloro-m-tolyl)-3-nitroguanidine or 1-(4-fluoro-m-tolyl)-3-nitroguanidine.

15. Guanidine compounds according to claim 3, wherein said compound is 1-(alpha-ethylbenzyl)-3-nitroguanidine or 1-nitro-3-(m-propoxybenzyl)guanidine.

* * * * *